(12) United States Patent
Sonehara et al.

(10) Patent No.: US 6,798,509 B2
(45) Date of Patent: Sep. 28, 2004

(54) METHODS AND INSTRUMENTS FOR FLUORESCENCE DETECTION

(75) Inventors: Tsuyoshi Sonehara, Kokubunji (JP); Kyoko Kojima, Hino (JP); Takashi Irie, Musashimurayama (JP)

(73) Assignee: Hitachi, Ltd., Tokyo (JP)

( * ) Notice: Subject to any disclaimer, the term of this patent is extended or adjusted under 35 U.S.C. 154(b) by 37 days.

(21) Appl. No.: 10/162,765

(22) Filed: Jun. 6, 2002

(65) Prior Publication Data

US 2003/0043374 A1 Mar. 6, 2003

(30) Foreign Application Priority Data

Aug. 20, 2001 (JP) ........................................ 2001-248480

(51) Int. Cl.[7] ............................................. G01N 21/00
(52) U.S. Cl. ...................................................... 356/344
(58) Field of Search .................................. 356/344, 413, 356/417; 204/451, 452, 601, 603; 250/200, 302, 458.1, 559.38; 435/91.2, 6

(56) References Cited

U.S. PATENT DOCUMENTS

| | | | | |
|---|---|---|---|---|
| 6,322,980 | B1 | * 11/2001 | Singh | 435/6 |
| 2002/0022226 | A1 | * 2/2002 | Nakao et al. | 435/6 |

FOREIGN PATENT DOCUMENTS

JP 53-40586 8/1976

OTHER PUBLICATIONS

D. Jed Harrison, Karl Fluri, Kur Seiler, Zhonghui Fan, Carlo S. Effenhauser, Andreas Manz, "Micromachining a Miniaturized Capillary Electrophoresis–Based chemical Analysis system on a Chip", Science, vol. 261, Aug. 13, 1993, pp. 895–897.

Alonso Castro and E. Brooks Shera, "Single–Molecule Electrophoresis", Analytical Chemistry, vol. 67, No. 18, Sep. 15, 1995, pp. 3181–3186.

H. John Crabtree, Martin U. Kopp and Andreas Manz, "Shah Convolution Fourier Transform Detection", Analytical Chemistry, vol. 71, No. 11, Jun. 1, 1999, pp. 2130–2138.

Carlos S. Effenhauser, Andreas Manz and H. Michael Widner, "Glass Chips for High–Speed Capillary Electrophoresis Separations with Submicrometer Plate Heights", American Chemical Society, Anal. Chem. 1993, 65, 2637–2642.

* cited by examiner

Primary Examiner—Tu T. Nguyen
(74) Attorney, Agent, or Firm—Reed Smith LLP; Stanley P. Fisher, Esq.; Juan Carlos A. Marquez, Esq.

(57) ABSTRACT

The disclosed invention provides methods and instruments for fluorescence detection making it possible to separate and detect analytes of a plurality of species in a migration (separation) channel with length of the order of millimeters. Analyte samples disperse across the whole detection region of a migration channel filled with a sieving matrix. Electrodes located in contact with a power supply and the sieving matrix cause the analytes to electophoretically migrate at predetermined velocity V. The detection region is irradiated by excitation light whose intensity changes in a cycle equaling pitch p in the direction that the analytes move. Fluorescence emission from the analytes exposed to the excitation light is detected by a detector. Fluctuation $\delta i(t)$ of output current from the detector is analyzed by a spectrum analyzer and the obtained spectrum is displayed. Florescence detection according to the invention is not affected by band broadening of analytes injected into the sample injection end of the migration channel.

5 Claims, 18 Drawing Sheets

METHODS AND INSTRUMENTS FOR FLUORESCENCE DETECTION

FIELD OF THE INVENTION

The present invention relates to methods and instruments for fluorescence detection for use in electrophoretic instruments and electrophoresis that are applied to analyzing biopolymers such as nucleotides and proteins.

BACKGROUND OF THE INVENTION

Electrophoresis in which to detect fluorescence by laser induction is widely used as one fundamental technique for analyzing biopolymers such as nucleotides and proteins because of its high sensitivity and convenience. In the biopolymer analysis field, capillary electrophoresis has lately been used commonly, superceding slab gel electrophoresis that was a mainstream analysis method. For the capillary electrophoresis, less Joule heating is generated when analytes electophoretically migrate and therefore high voltage can be used. As a result, analysis can be performed in a shorter time. The length of a migration (separation) channel is generally 50 cm to 20 cm. Aiming at reducing analysis time and downsizing the analysis system, diverse techniques have been developed to shorten the migration (separation) channel.

Such a method is described in Science, 261, 895–897 (1993) (prior art-1) that, by forming capillary channels on a substrate by application of photolithography technique and making analytes electrophoretically migrate through the channels, separating a plurality of fluorescence labeled amine acid is achieved with migration (separation) channel length of 0.75 cm to 2.2 cm.

Under conditions that unimolecular detection is performed, several species of deoxyribonucleic acid (DNA) can be separated in a migration (separation) channel with effective length of 0.25 mm, which is described in Anal. Chem., 67, 3181–3186 (1995) (prior art-2).

A method in which fluorescence emitted from analytes migrating through channels is sequentially detected through 55 300 μm-wide detection slits arranged at intervals of 700 μm and the velocity of the analytes is measured by Fourier transform of fluorescence intensity is described in Anal. Chem., 71, 2130–2138 (1999) (prior art-3).

A method in which interference fringes of excitation light are generated across analytes including fluorescent material and fluctuation of fluorescence radiated from the fluorescent material is measured in a correlation function, thereby measuring the fluid velocity of the analytes (one type of the method called Fluorescence Correlations (FCS)) is described in Kokai (Japanese Unexamined Patent Publication) No. Sho-53-40586 (No. 40586 of 1978) (prior art-4).

Using the analysis apparatus configured in the same way as for prior art 1, when the migration channel length is made shorter by 5 mm, the number of theoretical plates will be 5800, which is described in Anal. Chem., 65, 2637–2642 (1993) (prior art-5).

Under general conditions, electrophoresis of prior art posed the following problem. Band broadening of analytes injected into the sample inlet end of a channel in which electrophoresis takes place restricts separation of the analytes. When analytes with close mobilities are used, it is difficult to achieve good separation in a migration (separation) channel with length of the order of millimeters.

Actually, in prior art-1, a 2.2-cm long migration (separation) channel separates analytes with mobility difference of 10% or less, whereas a 0.75-cm long channel can separate only analytes with mobility difference of 20% or more.

Prior art-3 also presents problems. Detection slit pitch is restricted by the band broadening of injected analytes and cannot be reduced unlimitedly. The number of detection slits cannot be reduced arbitrarily because it influences separation performance. In prior art-3, the pitch (clearance) between detection slits is 0.7 mm, the number of detection slits is 55, and the effective migration (separation) channel length is about 4 cm which is longer than the channel length in prior art-1.

In prior art-1 and -3, because analytes in narrow band broadening are injected, it is necessary to form two or more crossing channels on the substrate.

Application of the FCS technique described in prior art-4 to the electrophoresis field has not been reviewed heretofore. The present invention is made through consideration of improving the FCS technique described in prior art-4 and applying it to electrophoresis.

SUMMARY OF THE INVENTION

The object of the present invention is to provide methods and instruments for florescence detection, enabling better separation and detection of a plurality of species of analytes with different mobility in a migration (separation) channel with length of the order of millimeters without being restricted by band broadening of the analytes injected into the sample injection end of the channel, thereby solving the above-described problems.

Methodology for fluorescence detection of the present invention is as follows. Analytes are caused to electophoretically migrate in a migration channel such that the analytes disperse in succession across a detection region where they are detected. Excitation light is applied to the detection region. The excitation light is controlled to have an intensity profile that periodically changes in a cycle equaling a pitch greater than the size of a analyte molecule in the direction that the analytes move (in the direction of electric field application). Instead, a slit is located between the detection region and a detector for detecting fluorescence. The slit is designed to have a transmittance profile that periodically changes in a cycle equaling a pitch greater than the size of a analyte molecule. For detected fluorescence emission from the analytes in the detection region, its power spectrum is obtained. Alternatively, an array sensor is used as the detector for detecting fluorescence and fluorescence emission from the detection region is measured. Distribution in the migration direction appears in the fluorescence measurements. Calculation is executed for the sum of the products of fluorescence intensity detected by the photoelectric elements of the array sensor and a function of predetermined pitch and the power spectrum as the sum of the products is obtained.

Description of the Principle Underlying the Invention

First, the principle underlying the invention is now described hereinafter. On the assumption that fluorescence labeled analytes of one species are irradiated by monochromatic excitation light, we consider that fluorescence emitted from the analytes exposed to the excitation light is detected by a photomultiplier (PM). Output current i (t) of the PM is expressed by mathematical expression 1 using molarity C(r, t) of analyte at time t and position r=(x, y, z), and the product I® of multiplying the following excitation light intensity at position r, and efficiency of collection of fluorescent light emitted from an analyte on the photoelectric plane of the PM.

Mathematical Expression 1

$$i(t) = \{ge\eta\epsilon\, Q\ln 10/(hc/\lambda)\} \int I(r)C(r,t)dr \quad \text{[Mathematical expression 1]}$$

where $dr=dxdydz$, $\epsilon$ is a molar excitation coefficient of analyte, Q is a fluorescence quantum yield of analyte, h is a plank constant, c is the velocity of light, $\lambda$ is wavelength of the excitation light, $\eta$ is quantum efficiency of the PM, e is elementary electric charge, g is current gain of the PM. By setting g=1, mathematical expression 1 can be applied to photodiodes. FCS (Fluorescence Correlations) is based on analysis of fluctuation $\delta i(t) = i(t) - \langle i(t)\rangle$ of $i(t)$ when the concentration distribution of the analytes stays in a thermal equilibrium state. In this relation, $\langle X(t)\rangle$ is an average in the ensemble of $X(t)$. A normalized auto-correlation function $G(t)$ that represents fundamental quantity of time dependency of fluctuation $\delta i(t)$ is defined by mathematical expression 2.

Mathematical Expression 2

$$G(t) = \langle \delta i(0)\delta i(t)\rangle / \langle (\delta i(t))^2\rangle \quad \text{[Mathematical expression 2]}$$

Furthermore, to analyze fluctuation $\delta i(t)$ in the frequency domain, a normalized power spectrum $S(\nu)$ of $\delta i(t)$ is defined as power spectrum $\delta i(t)/\langle(\delta i(t)^2\rangle^{1/2}$ (to be more precise, one-sided power spectrum). According to a Wiener-Khintchine theorem, $S(\nu)$ is expressed by mathematical expression 3. For integration $\int$, the lower limit is 0 and the upper limit is Mathematical Expression 3

$$S(\nu) = 4\int G(t)\cos(2\pi\nu t)dt \quad \text{[Mathematical expression 3]}$$

In the following, we will consider dispersion with a Gaussian envelope having width L ($e^{-2}$ wide) in the x-axis direction, sinusoidal oscillation by pitch p, and Gaussian profiles having width W ($e^{-2}$ wide) and H ($e^{-2}$ wide) in the y and z directions, respectively, as $I(r)$ that is expressed by mathematical expression 4, provided constraint that is specified in mathematical expression 5 shall be fulfilled.

Mathematical Expression 4

$$I(r) = I_0 \exp\{-8(x/L)^2\}\{\cos(2\pi x/p)+1\} \times \exp\{-8(y/W)^2\}\exp\{-8(z/H)^2\} \quad \text{[Mathematical expression 4]}$$

Mathematical Expression 5

$$1\,\mu m < p \ll L, W, H \quad \text{[Mathematical expression 5]}$$

For example, dispersion represented by $I(r)$ can be realized in this way. Create an interference pattern (fringes) by making two elliptic Gaussian beams that are symmetrical with regard to the y axis of the x-y plane on which the optical axis is placed intersect each other in a sample cell located in the vicinity of the origin. Detect fluorescence through slits having a Gaussian transmittance profile from the z-axis direction toward the y direction. If analytes move in the x-axis direction at a constant velocity V and constraint that is specified in mathematical expression 6 for a translational diffusion coefficient D of the analytes is fulfilled, $G(t)$ to be obtained from $I(r)$ in mathematical expression 4 is given by mathematical expression 7. Derivation of mathematical expression 7 will be fully described later.

Mathematical Expression 6

$$D \ll \nu/4 \quad \text{[Mathematical expression 6]}$$

Mathematical Expression 7

$$G(t) = (1/3)\{\cos(2\pi Vt/p)+1\} \times \exp\{-(2Vt/L)^2 - D(2\pi/p)^2 t\} + (2/3)\exp\{-(2Vt/L)^2\} \quad \text{[Mathematical expression 7]}$$

As implied by the first term of the right member of mathematical expression 7, $G(t)$ includes a component oscillating at frequency V/p in proportion to the velocity V of analyte. Thus, power spectrum $S(\nu)$ has a frequency peak proportional to the velocity of analyte. If the velocity V of analyte is determined, resulting from electrophoresis, the graph of $S(\nu)$ corresponds to a conventional electropherogram.

FIG. 1 is a schematic diagram for explaining the principle underlying the present invention. Analyte samples 1—1 to 1-N disperse across the whole detection region of a migration channel 2 filled with a sieving matrix (buffer solution, gel, polymers, etc.) Electrodes 4 and 5 located in contact with a power supply 3 and the sieving matrix cause the analytes to electophoretically migrate at predetermined velocity V. The detection region is irradiated by excitation light 6 whose intensity changes in a cycle equaling pitch p in the direction that the analytes move. Fluorescence emission from the analytes exposed to the excitation light is detected by a detector 7. Fluctuation $\delta i(t)$ of output current from the detector 7 is analyzed by a spectrum analyzer 8 and the obtained spectrum is displayed.

A typical method for approximately realizing periodically changing $I(r)$ as represented in mathematical expression 4 is roughly divided into the following three ways.

(1) Interference fringes are generated to cause periodical change in the intensity profile of excitation light as shown in FIG. 1.
(2) A slit with its transmittance changing periodically is installed between the detection region and the detector and fluorescence emission from the analytes is detected through the slit.
(3) An image sensor is used as the detector for detecting fluorescence and fluorescence intensity distributed in time and space is measured and profiled separately. Determine $C(r,t)$ and calculate the right member of mathematical expression 1 for $I(r)$ that changes periodically.

Description of Separation Efficiency in the Present Invention

If a plurality of species of analytes that move at different velocity is employed, the PM output current and its fluctuation will be the sum of photo current produced by each analyte and its fluctuation. If the analytes are sufficiently dilute and their mutual action is negligible, the power spectrum of the sum of fluctuation will be the sum of the power spectrum of fluctuation specific to each analyte. Thus, under proper conditions, peaks with different center frequency as many as the number of the analyte species can be separated and detected on the graph of $S(\nu)$. In the following, efficiency of analyte separation according to the methodology of the present invention will be discussed. In view hereof, the number of theoretical plates (NTP) is employed as an index of separation efficiency. NTP is defined by mathematical expression 8 using full width at half maximum (FWHM) of a peak that is positioned at V/p of $S(\nu)$.

Mathematical Expression 8

$$NTP = (8\ln 2)\{V/(p \times FWHM)\}^2 \quad \text{[Mathematical expression 8]}$$

As evident from mathematical expression 7, because $S(\nu)$ is Gaussian and Lorentzian convolution, it is difficult to represent FWHM analytically. Thus, first define coherence time $\tau_c$ as time at which the amplitude of the oscillating part in the first term of the right member of mathematical expression 7 becomes equaling $e^{-1}$. Then, approximate $S(\nu)$ by means of pure Gaussian Fourier transform having the same coherence time. According to this approximation, NTP is obtained by mathematical expression 9 where $p_0$ is defined by mathematical expression 10.

Mathematical Expression 9

$$(NTP)^{1/2} = 2^{1/2}\pi\tau_c V/p = \pi 2^{-1/2}(p/p_0)(L/p_0)/[1+\{1+(P/P_0)^4\}^{1/2}]$$ [Mathematical expression 9]

Mathematical Expression 10

$$p_0 = \pi(DL/V)^{1/2}$$ [Mathematical expression 10]

A curve shown in FIG. 2(A) represents a function of $(NTP)^{1/2}/(L/p_0)$ versus $p/p_0$. From this curve, to achieve good separation under the conditions that the parameters other than p are fixed, $p \neq p_0$ is desirable and the maximum separation efficiency is obtained when $(p/p_0) = 3^{1/4}$.

For example, assuming L=1 mm and $p=p_0=10\,\mu m$, $NTP \neq (L/p_0)^2/1.18$ is obtained from mathematical expression 9; that is, $NTP \neq 8470$ is attained, about 1.5 times the NTP of 5800 attained in a 5-mm migration channel in prior art-5.

For two peaks having equal FWHM, when the distance between the centers of the peaks is greater than $FWHM/(2\ln 2)^{1/2}$, the two peaks are generally defined as being completely separated in essence. When average mobility of two analytes is represented by $\mu_{AV}$ and mobility difference between them $\Delta\mu$, constraint that sets the conditions for achieving essentially complete separation of the two analytes having different mobility is expressed by mathematical expression 11. For example, if $\Delta\mu/\mu_{AV}=0.1$, $NTP \geq 3600$ must be fulfilled.

Mathematical Expression 11

$$NTP \geq 36(\mu_{AV}/\Delta\mu)^2$$ [Mathematical expression 11]

Description of Signal to Noise Ratio in the Present Invention

Next, signal to noise ratio (SNR) in the methodology of the present invention will be discussed. When an average number of molecules for the analytes detected is represented by N, we have mathematical expression 12.

Mathematical Expression 12

$$<\{\delta i(t)\}^2>=<\{i(t)\}^2>/N$$ [Mathematical expression 12]

The PM output current is input to a bandpass filter with pass-band width $\Delta v$ varying for a multiplicity of different center frequencies in a step for obtaining its power spectrum (at the present, actually, data sampling and discrete Fourier transform serve the function of such multi-filter). A root-mean-square of signal current $i_s(t)$ output by a filter for center frequency v is expressed by mathematical expression 13 where $<<\{X(t)\}^2>>$ represents the root-mean-square of $X(t)$.

Mathematical Expression 13

$$<<i_s(t)^2>>=<\{\delta i(t)\}^2><S(v)\Delta v$$ [Mathematical expression 13]

For shot noise current $i_{NS}(t)$ and thermal noise current $i_{NT}(t)$, their root-mean-squares are expressed by mathematical expressions 14 and 15, respectively, where e is elementary electric charge, $i_B(t)$ is the sum of dark current of the PM and photo current induced by background emission other than fluorescence, $k_B$ is a Boltzman constant, T is absolute temperature, and R is load resistance connected to the filter output. According to mathematical expressions 13 to 15, SNR is obtained by mathematical expression 16.

Mathematical Expression 14

$$<<\{i_{NS}(t)\}^2>>=2ge\{<i(t)>+<i_B(t)>\}\Delta v$$ [Mathematical expression 14]

Mathematical Expression 15

$$<<\{i_{NT}(t)\}^2>>=4k_B TR^{-1}\Delta v$$ [Mathematical expression 15]

Mathematical Expression 16

$$SNR=<<\{i_S(t)\}^2>>/[<<\{i_{NS}(t)\}^2>>+<<\{i_{NT}(t)\}^2>>]=<\{\delta i(t)\}^2>S(v)/\{2ge(<i(t)>+<i_B(t)>)+4k_B TR^{-1}\}$$ [Mathematical expression 16]

Assuming that $<<\{i_{NS}(t)\}^2>>>><<\{i_{NT}(t)\}^2>>$ and $<i(t)>>><i_B(t)>$ and using relation specified in mathematical expression 12, we have mathematical expression 17 where $i_M$ is defined by mathematical expression 18. $i_M$ is photo current induced at the cathode of the PM by fluorescence of one analyte species.

Mathematical Expression 17

$$SNR=S(v)i_M/(2e)$$ [Mathematical expression 17]

Mathematical Expression 18

$$i_M=<i(t)>/(gN)$$ [Mathematical expression 18]

From mathematical expression 18, when N is extremely great, SNR is constant, not depending on N, and its value is determined by photo current per molecule. By approximation in the same manner as for evaluating separation efficiency, a maximum value of S (v) where v>0, $S_{max} \neq S(V/p)$ is expressed by mathematical expression 19.

Mathematical Expression 19

$$S_{MAX}=\{\pi^{1/2}L/(6V)\} \times (p/p_0)^2/[1+\{1+(p/p_0)^4\}^{1/2}]$$ [Mathematical expression 19]

A curve shown in FIG. 2(B) represents dependency of $S_{max}$ normalized with $\{(\pi^{1/2}L/(6V)\}$ upon $p/p_0$. In view of SNR, $p \geq p_0$ is desirable. Thus, we have mathematical expression 20 as the most desirable condition for making separation efficiency compatible with SNR.

Mathematical Expression 20

$$p \neq p_0$$ [Mathematical Expression 20]

From FIGS. 2(A) and (B), to separate and detect different species of analytes without an extreme decrease of separation efficiency and SNR, constraint $1 \leq p/p_0 \leq 5$ must be fulfilled.

Detailed Description of Derivation of Mathematical Expression 7

In the following, derivation of mathematical expression 7 will be described in detail. Assuming that position vector r=r (x, y, z), dr=dxdydz, vector variable $q=q (q_x, q_y, q_z)$, $dq=dq_x dq_y dq_z$, and when spatial Fourier transform of I (r) is represented by I (q) that will be given in mathematical expression 21 and a correlation function of spatial Fourier transform of fluctuation in concentration $\delta C$ (r, t) that will be given in mathematical expression 22 is represented by F (q, t) that will be given in mathematical expression 23, we have mathematical expression 24. In mathematical expressions 21 and 22, j is imaginary unit.

Mathematical Expression 21

$$I(q)=17\, I(r)\exp(jq \cdot r)dr$$ [Mathematical Expression 21]

Mathematical Expression 22

$$\delta C(q, t)=\int \delta C(r, t)\exp(jq \cdot r)dr$$ [Mathematical Expression 22]

Mathematical Expression 23

$$F(q, t)=<\delta C(q, 0)\delta C(q, t)>$$ [Mathematical Expression 23]

Mathematical Expression 24

$$G(t)=\int |I(q)|^2 F(q, t)dq/\int |I(q)|^2 F(q, 0)dq$$ [Mathematical Expression 24]

In the following, for calculation convenience, $k=2\pi/p$, $\sigma_x=L/4$, $\sigma_y=W/4$, $\sigma_z=H/4$, $\tau_i=\sigma_i/D$ (i=x, y, z) are assigned. To redefine I (r) expressed in mathematical expression 7, by applying mathematical expressions 25 and 26, I (q) is expressed by mathematical expression 27.

Mathematical Expression 25

$$I_x(q_x)=(\pi/2)^{1/2}\sigma_x[\exp\{-0.5\sigma_x^2(q_x-k)^2\}+\exp\{-0.5\sigma_x^2(q_x+k)^2\}+, 2\exp\{-0.5(\sigma_x q_x)^2\}] \quad \text{[Mathematical expression 25]}$$

Mathematical Expression 26

$$I_i(q_i)= (2\pi)^{1/2}\sigma_i\exp\{-0.5(\sigma_i q_i)^2\}(i=y, z) \quad \text{[Mathematical expression 26]}$$

Mathematical Expression 27

$$I(q)=I_0 I_x(q_x)I_y(q_y)I_z(q_z) \quad \text{[Mathematical expression 27]}$$

By definition as is given in mathematical expression 28 using imaginary unit j, F (q, t) is obtained as in mathematical expression 29.

Mathematical Expression 28

$$F_x(q_x, t)=\exp(jq_x Vt-q_x^2 Dt), F_i(q_i, t)= \exp(-q_i^2 Dt) \, (i=y, z) \quad \text{[Mathematical expression 28]}$$

Mathematical Expression 29

$$F(q, t)= F(q, 0)F_x(q_x, t)F_y(q_y, t)F_z(q_z, t) \quad \text{[Mathematical expression 29]}$$

For q that is $|q|>10^6$ from mathematical expression 5, I (q) will be substantially 0 by evaluating mathematical expressions 25 and 26. For q that is $|q|>10^6$, F (q, 0) is regarded as constant, not depending on q, except for the vicinity of phase transition. Then, by defining $G_i$ (t) in mathematical expression 30, G (t) is obtained as in mathematical expression 31.

Mathematical Expression 30

$$G_i(t)=\int |I(q_i)|^2 F_i(q_i, t)dq_i/\int |I(q_i)|^2 F_i(q_i, 0)dq_i (i=x, y, z) \quad \text{[Mathematical expression 30]}$$

Mathematical Expression 31

$$G(t)=G(t)_x G(t)_y G(t)_z \quad \text{[Mathematical expression 31]}$$

From mathematical expression 25, $|I_x(q_x)|$ is obtained by mathematical expression 32, wherein because $\sigma_x k>>1$, the terms described within the brackets ([ ]) except the first three ones can be ignored. Then, by applying integration $\int$ with the lower limit of − and the upper limit of + and using imaginary unit j, B (k, t) is defined as in mathematical expression 33. From mathematical expressions 30 and 32, $G_x$ (t) is obtained by mathematical expression 34.

Mathematical Expression 32

$$|Ix(qx)|=(\pi/2)\sigma_x^2[\exp\{-\sigma_x^2(q_x-k)^2\}+\exp\{-\sigma_x^2(q_x-k)^2\}+\exp\{-\sigma_x^2-q_x^2\}+2\exp\{-\sigma_x^2(q_x-0.5k)^2-(\sigma_x k)^2/4\}+ 2\exp\{-\sigma_x^2(q_x+0.5k)^2-(\sigma_x k)^2/4\}] \quad \text{[Mathematical expression 32]}$$

$$B(k, t) = \int F_x(q, t)\exp\{\sigma_x^2(q-k)^2\}dq \quad \text{[Mathematical Expression 33]}$$

$$= \sigma_x^{-1}\{\pi/(1+(t/\tau_x))\}^{1/2} \times$$

$$\exp[\{jkVt-k^2Dt-(Vt/(2\sigma_x))^2\}/ (1+(t/\tau_x))]$$

Mathematical Expression 34

$$G_x(t)=\{B(k, t)+B(-k, t)+4B(0, t)\}/ \{B(k, 0)+B(-k, 0)+4B(0, 0)\} \quad \text{[Mathematical expression 34]}$$

Because $\sigma_x<<V/\tau_x$ from mathematical expression 4, approximation of mathematical expression 33 can be performed as in mathematical expression 35 where j is imaginary unit.

Mathematical Expression 35

$$B(k, t)=\pi^{1/2}\sigma_x^{-1}\times\exp[jkVt-k^2Dt-\{Vt/(2\sigma_x)\}^2] \quad \text{[Mathematical expression 35]}$$

From mathematical expressions 34 and 35, $G_x$ (t) is obtained by mathematical expression 36.

Mathematical Expression 36

$$G_x(t)=(\tfrac{1}{3})\exp[-k^2Dt-\{Vt/(2\sigma_x)\}^2]\times\{\cos(2\pi Vt/P)+1\}+ (\tfrac{2}{3})\exp[\{Vt/(2\sigma_x)\}^2] \quad \text{[Mathematical expression 35]}$$

The right member of mathematical expression 36 is the same as the right member of mathematical expression 7. Meanwhile, $G_y$ (t) and $G_z$ (t) are directly obtained from mathematical expressions 26, 28, and 30 and $G_i$ (t) is expressed by mathematical expression 37. Because $1/(k^2 D)$ $<<\tau_i$ (i=y, z) from mathematical expression 5, $G_y$ (t) and $G_z$ (t) can be regarded as being 1 with regard to t before $G_x$ (t) vanishes. Hence, from mathematical expressions 36 and 37, we can get mathematical expression 7.

Mathematical Expression 37

$$G_i(t)=\{(1+(t/\tau_i)\}^{-1/2}(i=y, z) \quad \text{[Mathematical expression 35]}$$

DETAILED DESCRIPTION OF THE PREFERRED EMBODIMENTS

Figure 1:
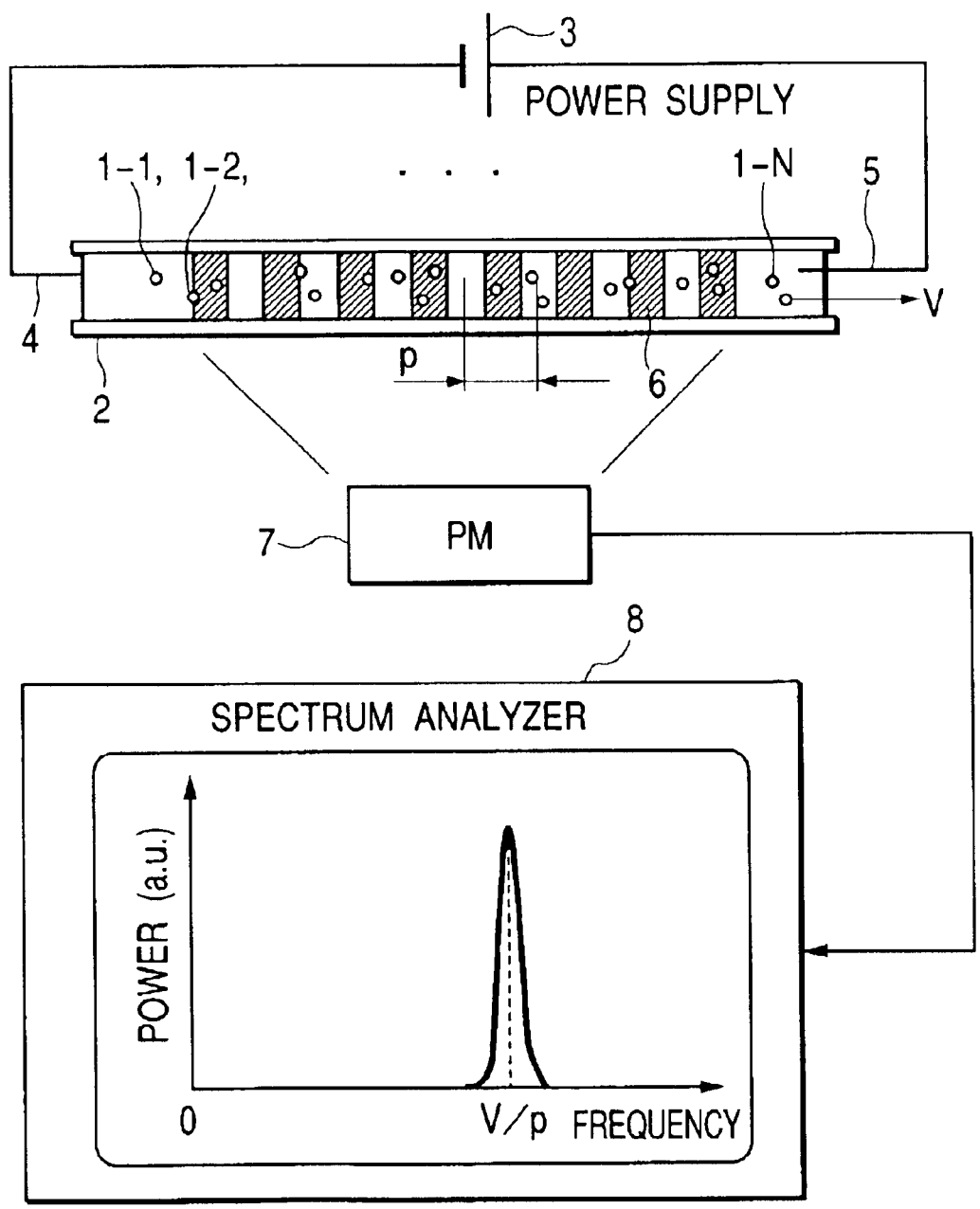
FIG. 1 is a schematic diagram for explaining the principle underlying the present invention.
Figure 2A:
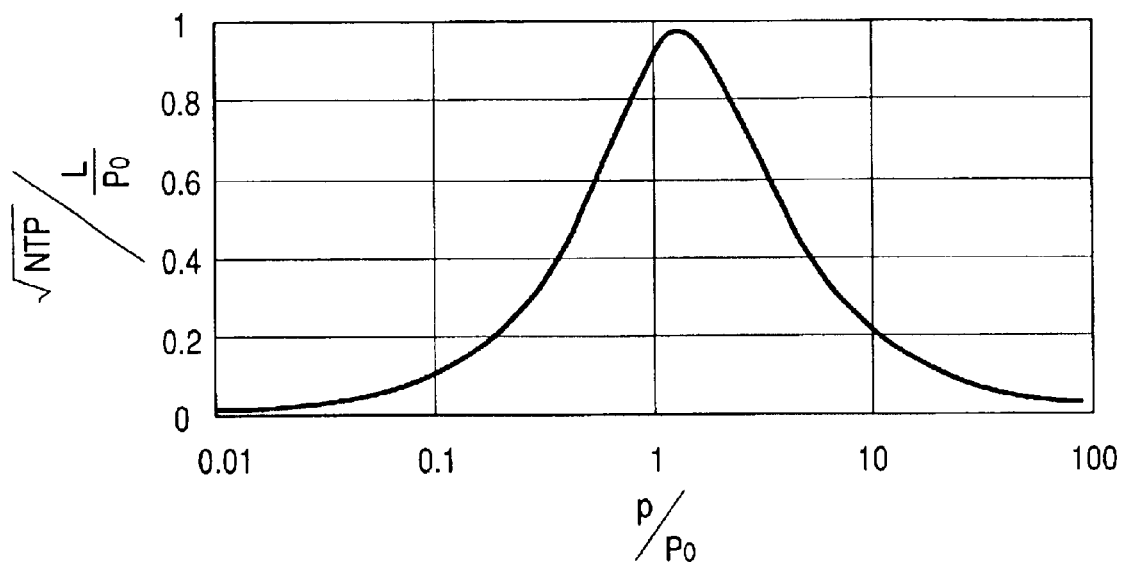
FIG. 2 shows (A) separation efficiency and (B) signal-to-noise ratio curves obtained by fluorescence detection methodology of the present invention, the separation efficiency and SNR depending on a pitch of intensity profile of excitation light.
Figure 2B:
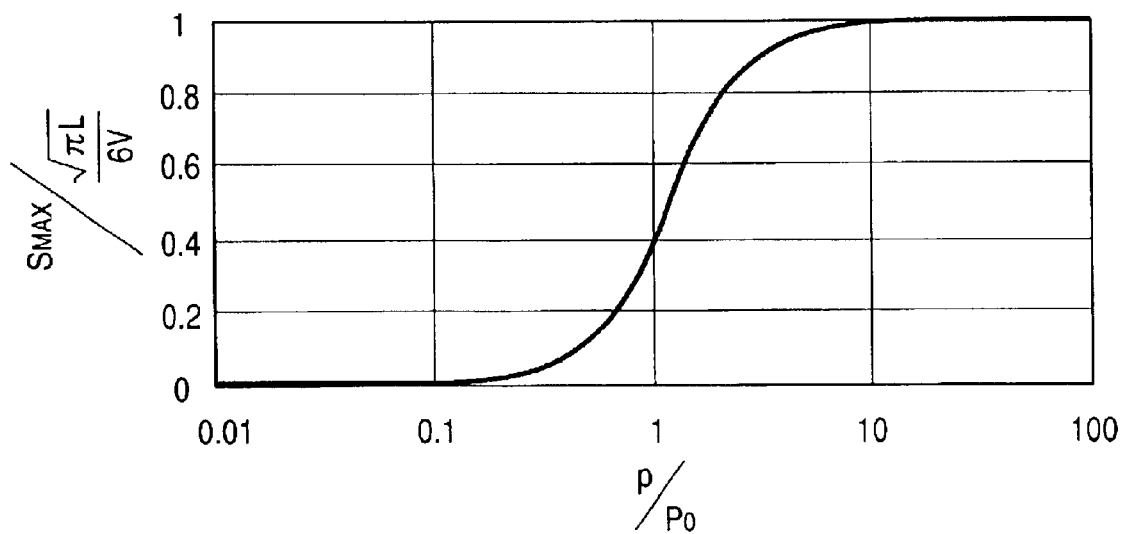

A method for fluorescence detection of the present invention is built, as first constitution, by making a plurality of charged analytes having different mobility electrophoretically migrate by electric field application in a sieving matrix, applying excitation light that is controlled to have an intensity profile that periodically changes in the direction that the analytes move to a region across which the analytes disperse in succession in the sieving matrix with their concentration distribution staying in a thermal equilibrium state, detecting fluorescence emission from the analytes, and obtaining a power spectrum of fluctuation of detected fluorescence intensity. The above intensity profile is created by splitting the excitation light radiated from a single light source into two diverging beams and making the two beams intersect and interfere with each other in the above region. Alternatively, the intensity profile is created by scanning the above region with the excitation light in cycles of a predetermined frequency in an angled direction in which to apply the excitation light to the region and making the excitation light blink in cycles of a frequency that is an integral multiple of the predetermined frequency. When a translational diffusion coefficient of the analytes is represented by D, migration velocity of the analytes V, length of the region irradiated by the excitation light in the migration direction of the analytes L, and pitch of the intensity profile of the excitation light p, p is determined such that $p \neq \pi (DL/V)^{1/2}$.

A method for fluorescence detection of the present invention is built, as second constitution, by making a plurality of charged analytes having different mobility electrophoretically migrate by electric field application in a sieving matrix, applying excitation light to a region across which the analytes disperse in succession in the sieving matrix with their concentration distribution staying in a thermal equilibrium state, converging a fluorescence image generated by fluorescence emission from the analytes on a slit that is designed to have a transmittance profile that periodically changes in the direction that the analytes move and detecting the fluorescence image, and obtaining a power spectrum of fluctuation of detected fluorescence intensity. When a translational diffusion coefficient of the analytes is represented by D, migration velocity of the analytes V, length of the region irradiated by the excitation light in the migration direction of the analytes L, magnifying power of the fluorescence image to be detected M, and pitch of the transmittance profile of the slit p, p is determined such that $p \neq \pi M(DL/V)^{1/2}$.

A method for fluorescence detection of the present invention is built, as third constitution, by making a plurality of charged analytes having different mobility electrophoretically migrate by electric field application in a sieving matrix, applying excitation light to a region across which the analytes disperse in succession in the sieving matrix with their concentration distribution staying in a thermal equilibrium state, detecting a fluorescence image generated by fluorescence emission from the analytes by using an array sensor having a plurality of pieces (assumed to be N) of photoelectric elements arranged in the direction that the analytes move, and obtaining a power spectrum in the aggregate of the photoelectric elements in such a manner that, when fluorescence intensity detected by the i-th one of the photoelectric elements arranged in the migration direction is represented by $q_i$ and a function of predetermined pitch is f (Ki) where K is a constant including an absolute value of 1 and i is a variable, the sum of products $Q=\Sigma q_i f$ (Ki) for i=1, 2, . . . , N is calculated. When a translational diffusion coefficient of the analytes is represented by D, migration velocity of the analytes V, length of the region irradiated by the excitation light in the migration direction of the analytes L, pitch of intervals at which the photoelectric elements are arranged $p_1$, magnifying power of the fluorescence image to be detected M, and pitch of the function of predetermined pitch f (Ki) is $p_2$, $p_1 p_2$ is determined such that $p_1 p_2 \neq \pi M(DL/V)^{1/2}$. A plurality of migration channels across which the analytes electophoretically migrate are placed in parallel on a same plane at least in part thereof and the parallel migration channels are irradiated orthogonally by the excitation light from the direction parallel with or perpendicular to the above plane.

An instrument for fluorescence detection of the present invention comprises, as first constitution, a migration channel across which a plurality of charged analytes having different mobility are caused to electophoretically migrate by electric field application in a sieving matrix, a light source emitting excitation light, means for applying excitation light that is controlled to have an intensity profile that periodically changes in the direction that the analytes move to a region across which the analytes disperse in succession in the sieving matrix with their concentration distribution staying in a thermal equilibrium state, and means for detecting fluorescence emission from the analytes. The power spectrum of fluctuation of detected fluorescence intensity is obtained through calculation by an arithmetic unit. The above instrument includes light-splitting means for splitting the excitation light radiated from a single light source into two diverging beams and the above intensity profile is created by making the two beams intersect and interfere with each other in the above region. Alternatively, the intensity profile is created by means for scanning the above region with the excitation light in cycles of a predetermined frequency in an angled direction in which to apply the excitation light to the region and means for making the excitation light blink in cycles of a frequency that is an integral multiple of the predetermined frequency. When a translational diffusion coefficient of the analytes is represented by D, migration velocity of the analytes V, length of the region irradiated by the excitation light in the migration direction of the analytes L, and pitch of the intensity profile of the excitation light p, p is determined such that $p \neq \pi (DL/V)^{1/2}$.

An instrument for fluorescence detection of the present invention comprises, as second constitution, a migration channel across which a plurality of charged analytes having different mobility are caused to electophoretically migrate by electric field application in a sieving matrix, a light source emitting excitation light that is applied to a region across which the analytes disperse in succession in the sieving matrix with their concentration distribution staying in a thermal equilibrium state, lenses for converging a fluorescence image generated by fluorescence emission from the analytes on a slit that is designed to have a transmittance profile that periodically changes in the direction that the analytes move, and a detector for detecting the fluorescence image, wherein the slit is located between the region and the detector. The power spectrum of fluctuation of detected fluorescence intensity is obtained through calculation by an arithmetic unit. When a translational diffusion coefficient of the analytes is represented by D, migration velocity of the analytes V, length of the region irradiated by the excitation light in the migration direction of the analytes L, magnifying power of the lenses M, and pitch of the transmittance profile of the slit p, p is determined such that $p \neq \pi M(DL/V)^{1/2}$.

An instrument for fluorescence detection of the present invention comprises, as third constitution, a migration channel across which a plurality of charged analytes having different mobility are caused to electophoretically migrate by electric field application in a sieving matrix, a light source emitting excitation light that is applied to a region across which the analytes disperse in succession in the sieving matrix with their concentration distribution staying in a thermal equilibrium state, an array sensor having a plurality of pieces (assumed to be N) of photoelectric elements arranged in the direction that the analytes move and detecting an fluorescence image generated by fluorescence emission from the analytes, and an arithmetic unit for obtaining a power spectrum in the aggregate of the photoelectric elements in such a manner that, when fluorescence intensity detected by the i-th one of the photoelectric elements arranged in the migration direction is represented by $q_i$ and a function of predetermined pitch is f (Ki) where K is a constant including an absolute value of 1 and i is a variable, the sum of products $Q = \Sigma q_i f(Ki)$ for $i = 1, 2, \ldots, N$ is calculated. When a translational diffusion coefficient of the analytes is represented by D, migration velocity of the analytes V, length of the region irradiated by the excitation light in the migration direction of the analytes L, pitch of intervals at which the photoelectric elements are arranged $p_1$, magnifying power of the fluorescence image to be detected M, and pitch of the function of predetermined pitch f (Ki) is $p_2$, $p_1 p_2$ is determined such that $p_1 p_2 \neq \pi M(DL/V)^{1/2}$. The above instrument includes a plurality of migration channels placed in parallel on a same plane at least in part thereof and the parallel migration channels are irradiated orthogonally by the excitation light from the direction parallel with or perpendicular to the above plane.

An instrument for fluorescence detection of the present invention comprises, as fourth and fifth constitution, a plurality of migration channels placed in parallel on a same plane at least in part thereof, across each of which a plurality of charged analytes having different mobility are caused to electophoretically migrate by electric field application in a sieving matrix, and a light source emitting excitation light that is applied to a region across which the analytes disperse in succession in the sieving matrix with their concentration distribution staying in a thermal equilibrium state.

The instrument for fluorescence detection of the present invention as the fourth constitution further includes a two-dimensional detector having a plurality of pieces (assumed to be N) of photoelectric elements arranged in the direction that the analytes move and detecting an fluorescence image generated by fluorescence emission from the analytes passing through the parallel migration channels that are irradiated orthogonally by the excitation light from the direction parallel with or perpendicular to the plane on which the channels run and an arithmetic unit for obtaining a power spectrum in the aggregate of the photoelectric elements in such a manner that, when fluorescence intensity detected by the i-th one of the photoelectric elements arranged in the migration direction is represented by $q_i$ and a function of predetermined pitch is f (Ki) where K is a constant including an absolute value of 1 and i is a variable, the sum of products $Q = \Sigma q_i f(Ki)$ for $= i 1, 2, \ldots, N$ is calculated.

The instrument for fluorescence detection of the present invention as the fifth constitution further includes a two-dimensional detector which consists of N2 ($N2 \geq 2$) arrays arranged in a direction intersecting orthogonally the direction that the analytes move, each array consisting of $N_1$ ($N_1 \geq 2$) pieces of photoelectric elements arranged in the direction that the analytes move, and detects an fluorescence image generated by fluorescence emission from the analytes passing through the parallel migration channels that are irradiated orthogonally by the excitation light from the direction parallel with or perpendicular to the plane on which the channels run, lenses for converging the fluorescence image on area where the photoelectric elements are arranged, and an arithmetic unit for obtaining a power spectrum in the aggregate of the photoelectric elements in such a manner that, when fluorescence intensity detected by one of the two-dimensionally arranged photoelectric elements that is placed in the i-th position in the direction that the analytes move and the j-th position in the direction intersecting orthogonally the direction that the analytes move is represented by $q_{ij}$ and a function of predetermined pitch is f (Ki) where K is a constant including an absolute value of 1 and i is a variable, the sum of products $Q = \Sigma q_{ij}$ for i and j that fulfill constraints $1 \leq i \leq N_1$ and $n_1 \leq j \leq n_2$, where $n_1$ and $n_2$ are integers fulfilling constraint $1 \leq n_1 \& 1t; n_2 \leq N_2$, is calculated.

According to the constitutions of the present invention, velocity at which analytes migrate can be determined only by fluorescence intensity measurement. It is unnecessary to make analytes electophoretically migrate over a long distance from the sample injection point to the sample detection point, which would otherwise be required in the previous electrophoresis method. Because the invention avoids degrading electrophoresis and separation due to band broadening of analytes injected into the sample injection end of a migration channel, realizing significantly shorter migration channels can be expected.

The methods and instruments for fluorescence detection of the present invention are suitably applied to fluorescence process and apparatus for analyzing charged biopolymers including nucleotides such as DNA and RNA or nucleotide fragments, amino acids, protein, etc. and neutral molecules such as sugar into which molecules of charged fluorophores and the like are combined.

Embodiment 1

Figure 3:
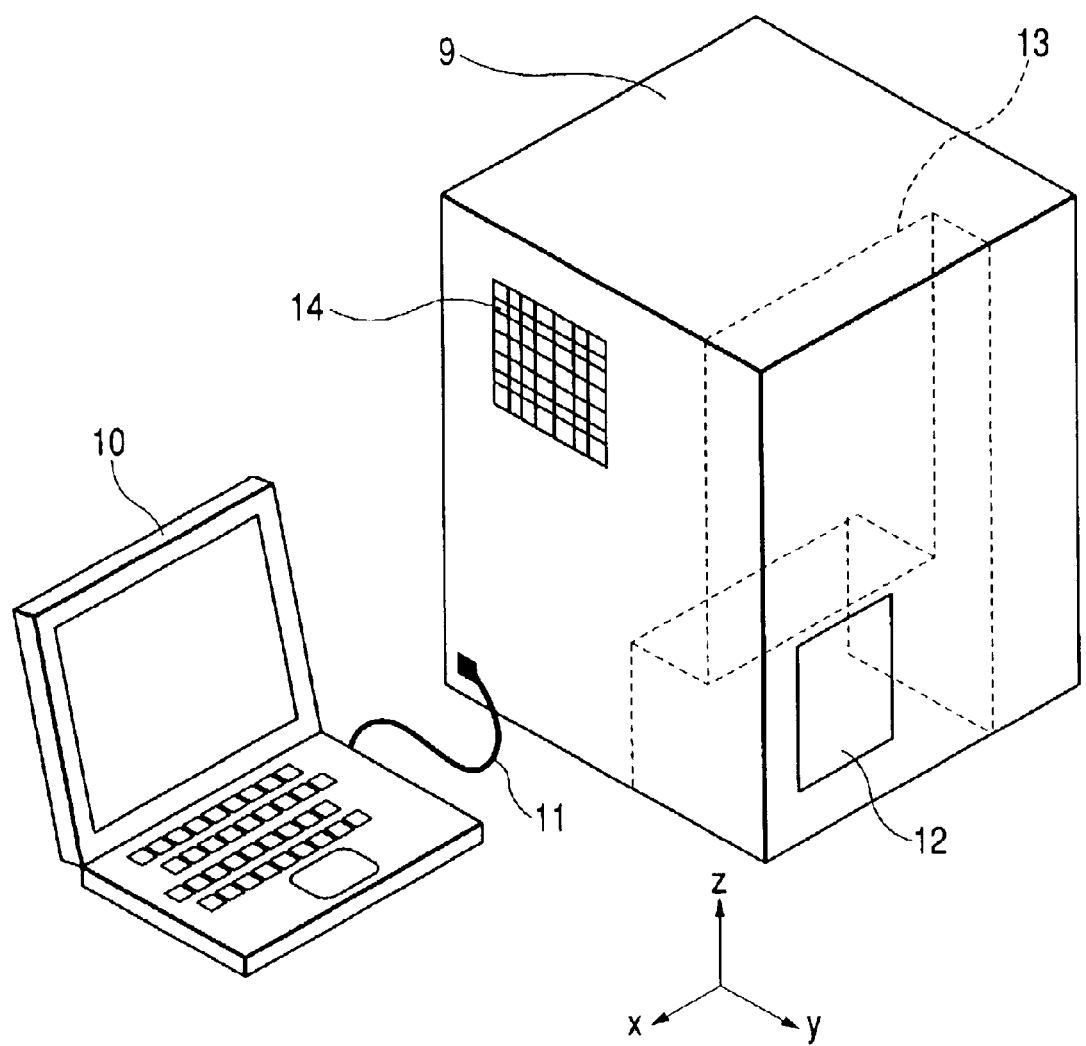
FIG. 3 shows the appearance of an instrument for florescence detection embodied as a preferred Embodiment 1 of the present invention.

FIG. 3 shows the appearance of an instrument for florescence detection embodied as a preferred Embodiment 1 of the present invention. The body of the instrument 9 has a box shape and its internal space is divided into two blocks by bulk heading 13 which is drawn with dash lines. In one block (sample room) including the door 12, analytes, a migration channel, and a sieving matrix are placed and this room is temperature controlled. In the other block, the light source, its power supply, a unit for controlling communication with a computer, motor controller, and other components are installed. Heat generated by the light source is radiated through an exhaust hole 14. The instrument body 9 is connected to a personal computer 10 by a cable 11 and data communication via the cable 11 for instrument control is performed. Data is analyzed by a processor inside the personal computer 10 and the result of analysis is presented on the display of the computer. For explaining Embodiment 1 in detail, we use a system of x, y, and z coordinates for the x, y, and z axes parallel with the corresponding edges of the instrument body as denoted in FIG. 3. The x-z plane is parallel with the plane which contains the optical axis of the excitation light beams and the migration channel center axis.

Figure 4:
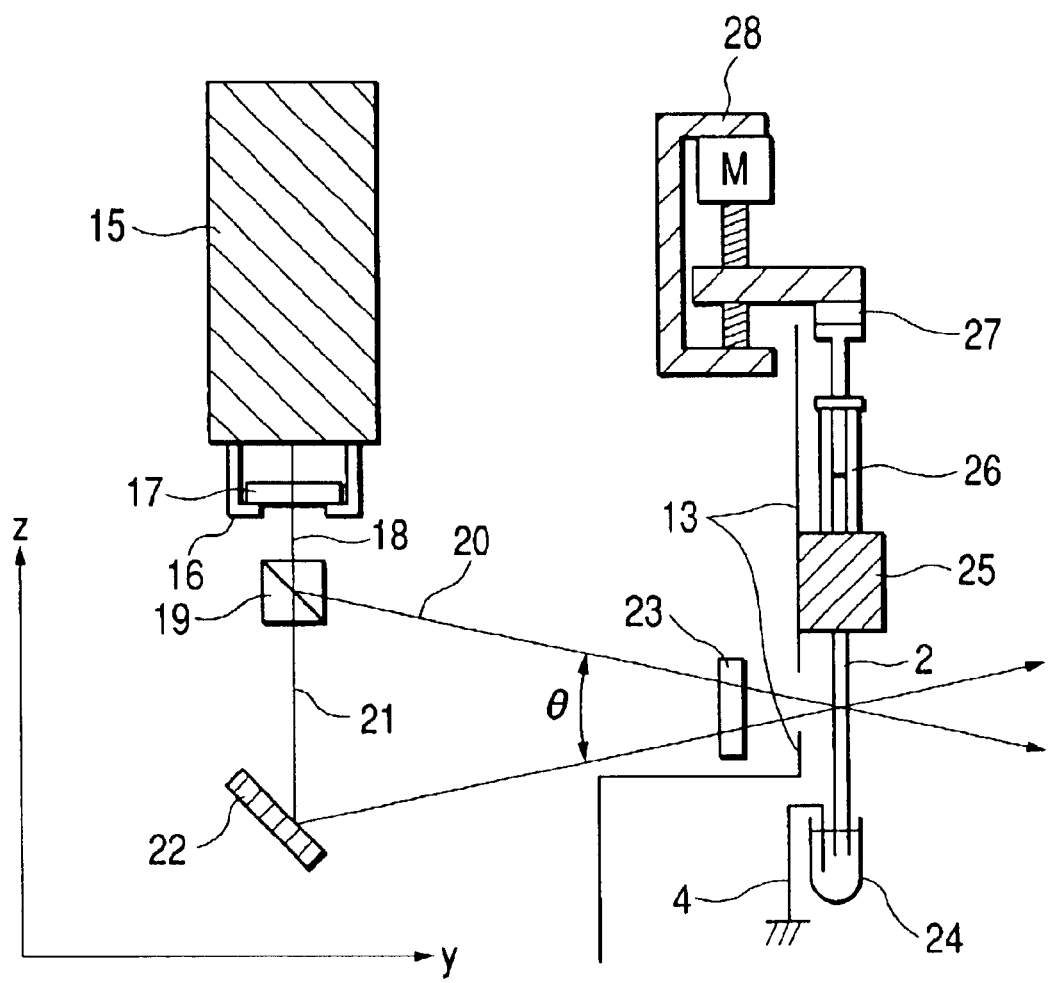
FIG. 4 shows a cross section of the instrument body of Embodiment 1 of the present invention.

FIG. 4 shows a cross section of the instrument body 9 of Embodiment 1, in parallel with the y-z plane and along the optical axis of the excitation light beams, viewed from the X-axis direction. The light source 15 is an argon ion laser capable of generating light with wavelength of 488 nm and output of 10 mW. Light from the light source 15 passes through a filter 17 allowing only light with wavelength of 488±10 nm to pass. The light passing through the filter is used as excitation light 18. The filter 17 is mounted to the light source 15 by a holder 16. The excitation light 18 is subjected to amplitude division at 1:1 of intensity ratio by a beam splitter 19. A transmitted beam 21 passing through the beam splitter is reflected by a mirror 22 and intersects a reflected beam 20 reflected by the beam splitter at a point in a migration channel 2, when interference fringes are generated thereby. The migration channel is formed within a capillary of square quarts and its cross section consists of an inner square of 75-$\mu$m long edges and an outer square of 350-$\mu$m long edges. The entire length of the migration channel is 30 mm and the capillary is installed so that analytes will move in the z-axis direction.

Distance from the bottom end of the capillary to the radiation point of the excitation light, that is, the fluorescence detection point (detection region) is 10 mm. The diameter of the reflected beam 20 and the transmitted beam 21 is narrowed by a cylindrical lens 23 in the direction (of the x axis) in which the beams intersect the migration channel orthogonally so that the beams will be efficiently applied to the migration channel. The light source 15 outputs collimated beams with a diameter of 1 mm (diameter of $e^{-2}$). The focus distance of the cylindrical lens is 50 mm. The intensity profile of the cross section of the excitation beams on the migration channel is elliptic Gaussian in which the diameter (diameter of $e^{-2}$) is 1 mm in the z direction and 50 $\mu$m in the x direction. The power of the excitation light applied to the migration channel becomes 7 mW because of the loss for the filter and lenses.

The bottom end of the capillary 2 is immersed in a solution including a predetermined concentration of samples 24 and connected to an electrode 4 via the solution of the samples 24. The top end of the capillary is connected to a syringe 26 filled with the sieving matrix via a bifurcation block 25. When the syringe 20 is pushed by an automatic translation stage 28 equipped with a stepping motor, the capillary is charged with the sieving matrix from the syringe. A pressure sensor 27 is installed between the syringe 26 and the automatic translation stage 28. The pressure sensor monitors the pressure at which the capillary is charged with the sieving matrix under the control of the motor controller and feeds back the monitored pressure to the controller to keep a constant pressure. In consequence, the capillary 2 is charged with the sieving matrix by constant force of a predetermined pressure. Because the entire length of the capillary is very short, namely, 30 mm, by charging of the matrix for 20 seconds at pressure of 1 kgf, if a 3% polyacrylamide solution is employed as the sieving matrix, the capillary can be charged with the sieving matrix of quantity 8 times as much as the displacement volume of the capillary. In the following explanation, the bottom end of the capillary will be referred to as a sample injection end and its top end a sieving matrix injection end.

Figure 5:
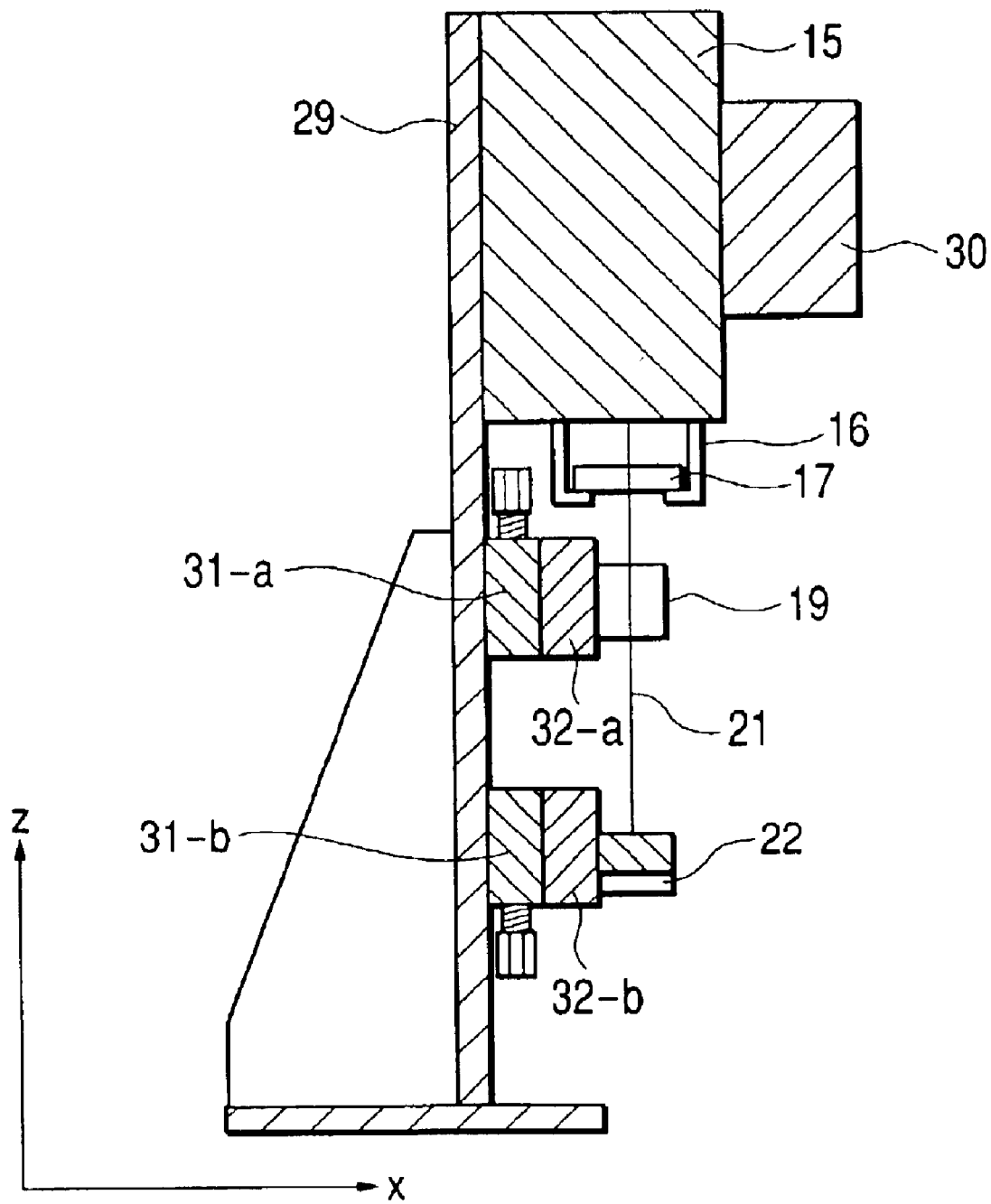
FIG. 5 shows another cross section of the instrument body of Embodiment 1 of the present invention.

FIG. 5 shows a cross section of the instrument body 9 of Embodiment 1, in parallel with the x-z plane and along the optical axis of the excitation beam 21, viewed from the negative direction of the y axis. The light source 15 is installed to a bracket 29 so that it will output light downward at a right angle. The beam splitter 19 is mounted to a rotation stage 32-*a* that is mounted on a translation stage 31-*a*. The mirror 22 is mounted to a rotation stage 32-*b* that is mounted on a translation stage 31-*b*. Through these stages, the positions and angles of the beam splitter 1 and the mirror 22 can be adjusted by fine control. The positions and angles of the beam splitter 1 and the mirror 22 are adjusted so that the bisector of an angle formed by the optical axis of the reflected beam 20 reflected by the beam splitter and the optical axis of the transmitted beam 21 passing through the beam splitter 19 and reflected by the mirror 22 will be vertical to the migration channel 2. In this state, pitch p of the interference fringes on the migration channel is given by mathematical expression 38, independent of the refractive index of the capillary and the sieving matrix.

Mathematical Expression 38

$$p=\lambda/(2 \sin (\theta/2)) \qquad \text{[Mathematical expression 38]}$$

Angle $\theta$ is an angle formed in the air by the optical axis of the reflected beam 20 reflected by the beam splitter and the optical axis of the transmitted beam 21 passing through the beam splitter 19 and reflected by the mirror 22. In Embodiment 1, angle $\theta$ may be set at any value in a range from 1.5° to 6°. As a result, pitch p can be set successively in a range of from about 5 $\mu$m to 20 $\mu$m. The heat generated by the light source 15 is radiated by a fan 30.

Figure 6:
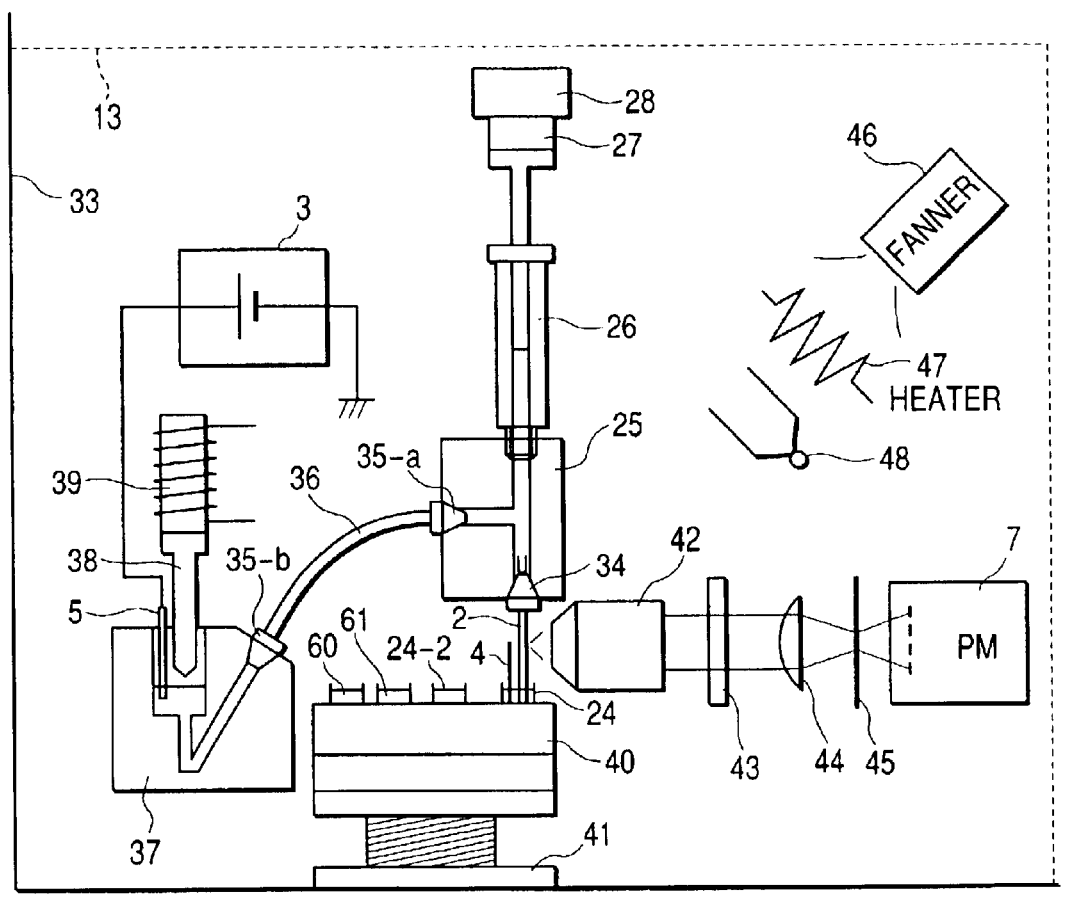
FIG. 6 is a view for explaining the interior of a sample room of the instrument body of Embodiment 1 of the present invention.

FIG. 6 shows the interior of the sample room of the instrument body 9, viewed from the front (in the y-axis direction) with the door 12 being open. The sample room is surrounded by the outer wall 33 of the instrument body and the bulk heading inside the instrument. In the sample room, wind generated by a fanner 46 always circulates and temperature keeps constant.

When sample analysis begins, the wind temperature is controlled to be a temperature set on the personal computer by means of a heater 47 and a temperature sensor 48. The temperature sensor 48 is a platinum thermosensor. The bifurcation block 25 not only connects the syringe 26 and the capillary 2 via a fitting 34, but also connects a buffer tank 37 to the sieving matrix injection end of the capillary 2 by the T branch pipe in its center via a tube 36 and nipples 35-*a* and 35-*b*. The buffer tank is filled with buffer solution for electrophoresis and installed so that an electrode 5 will be immersed in the buffer solution. High positive voltage is applied to the electrode 5, samples (analytes) are injected, and electrophoresis is performed. The buffer solution for electrophoresis employed in Embodiment 1 is TBE containing 89-mM Tris, 89-mM borate, and 1-mM EDTA.

Because, in Embodiment 1, deoxyribonucleic acids (DNA) that are negative ions are primary objects to be analyzed, setup is performed so that the electrode 5 connected to the sieving matrix injection has positive potential in opposition to the electrode 4 at the sample injection end. However, if positively charged samples are analyzed, the polarity of voltage to be applied should be inverted.

The passage in the buffer tank is controlled to open and close by a piston 38 fixed to a solenoid 39. The passage closes during sieving matrix injection and opens during electrophoresis. Samples 24, 24-2 to be analyzed are placed on an automatic rotation stage 40 and automatic z-stage 41. The automatic rotation stage 40 has holes for enabling 24 samples, a washing water jar 60, and a water jar for waster sieving matrix 61 to be arranged on the circumference with a diameter of 100 mm.

By up and down movement of the automatic z-stage 41 and rotation of the automatic rotation stage 40 in conjunction with the automatic translation stage 28, cleaning the sample injection end of the capillary, charging the capillary with sieving matrix, and analyzing up to 24 samples can be performed automatically. Holes in which samples are set are assigned numbers 1 to 24 and these numbers will be referred to as sample numbers hereinafter.

Fluorescence emitted from the analytes in the capillary are collected by a lens 42 and formed into collimated beams which then pass through a filter 43 that allows only the wavelength component of fluorescence to pass and blocks out the excitation light. A lens 44 converges the beams on a slit 45, thus making a real image on the slit. In Embodiment 1, the transmission bandwidth of the filter 43 is 510–560 nm and can be used suitably for samples labeled with florescent coloring matters including fluorescein, thiazole orange, and oxazole yellow. The slit 45 is a 0.1-mm thick stainless plate with a long and narrow hole parallel with the center axis of the capillary. The slit blocks out scattered light by the reflection of the excitation light on the surface of the capillary and allows fluorescence from the analytes to pass.

For the lens set of two lenses 42 and 44, its magnifying power is 20 times as much and the numerical aperture is 0.4. For the size of a capillary image to be obtained on the slit, the width across its outer walls is 7.2 mm and the width of the inner migration channel is 1.5 mm. In order to well block out the scattered light at the outer walls and allow the fluorescence from the migration channel to pass efficiently, the hole width of the slit is 4 mm, considering the effect of burring and astigmatism of the lens set. The light passing through the slit 45 is detected by the detector 7. The detector 7 is a head-on-type photomultiplier (PM) Its quantum efficiency is about 10%, current gain is about 500,000 times as much, and photosensitive surface area is a circle with a diameter of 25 mm.

Figure 7:
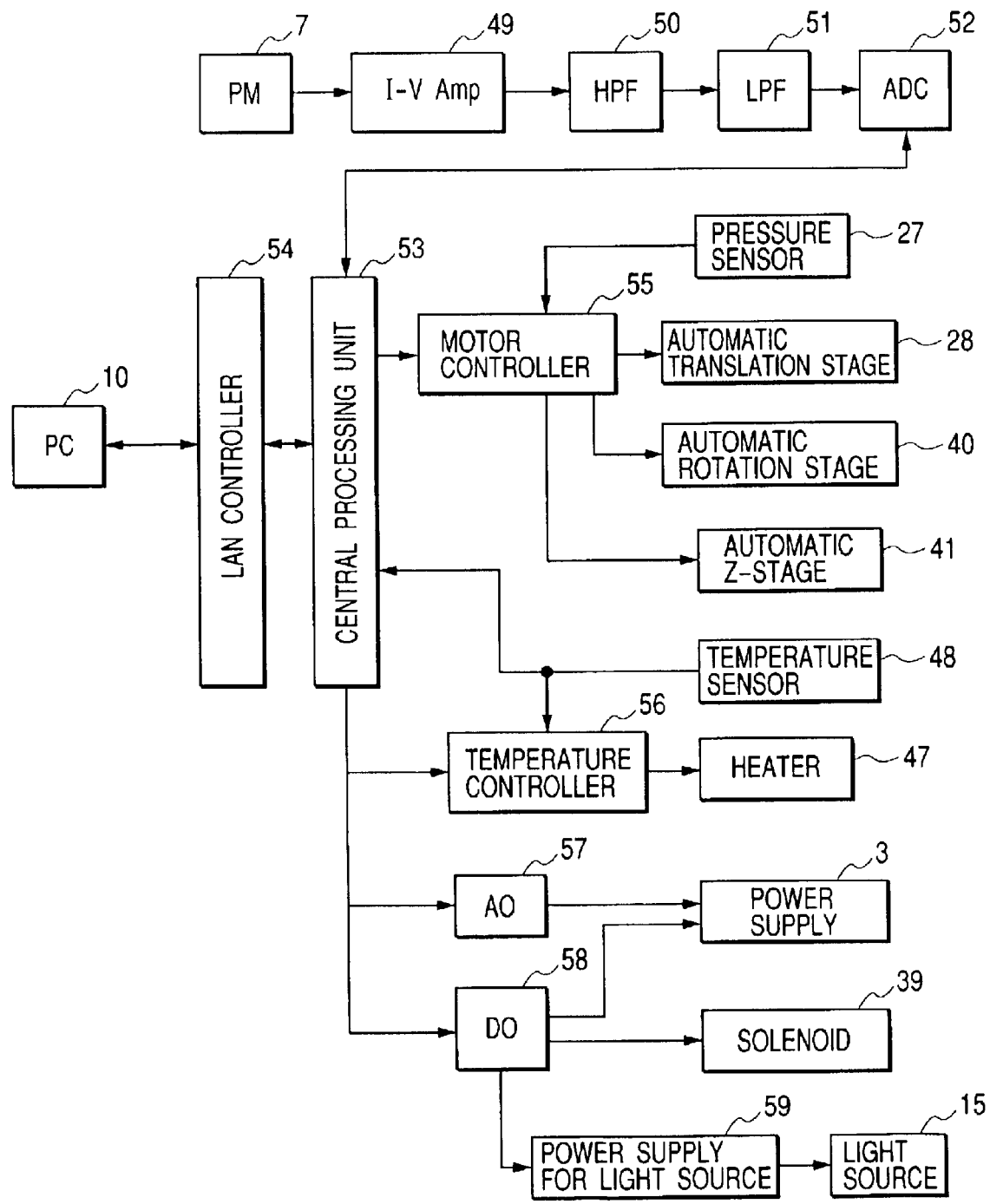
FIG. 7 shows a systematic operation flow regarding output signal processing of the detector and control of automatic stages in Embodiment 1 of the present invention.

FIG. 7 shows a systematic operation flow regarding output signal processing of the detector and control of the automatic stages and the like in Embodiment 1. Output current from the detector 7 is converted into a voltage signal by a current-voltage converter 49. The voltage signal is input to a high-pass filter 50 and its DC component is cut off. The signal is further input to a low-pass filter 51 and its frequency range is restricted to a bandwidth. Then, the signal is digitized with 16-bit resolution at sampling frequency of 250 Hz by an analog-digital conversion unit 52.

The gain of the current-voltage converter 49 is $10^6$ V/A. The high-pass filter 50 also serves as an AC-coupling amplifier and its gain is 20±0.5 dB in a range of 0.2 Hz to 50 kHz. The low-pass filter is a coalition Chebychev type of degree eight and its gain is flat within ±0.2 dB in a range of DC to 96 Hz and −80 dB or below at 150 Hz or higher, and alias at or below 100 Hz at the sampling frequency of 250 Hz is suppressed to −80 dB or below. Effective in the frequency range of 0.2 Hz to 96 Hz, therefore, spectrum analysis in an 80-dB dynamic range can be performed with accuracy to ±0.7 dB.

The digital signal from the analog-digital conversion unit 52 is transferred to a central processing unit 53 integrated in the instrument 9 and from which the signal is further transferred via a LAN controller 54 to the memory of the personal computer 10. The microprocessor of the personal computer 10 calculates a power spectrum of fluctuation of the PM output current, based on a predetermined number of supplied digital signals (data) which must have been set by the user, and outputs the result of calculation to the display.

In Embodiment 1, the power spectrum is obtained as a square of the absolute value given by Fourier transform of a sequence of digital signals (data) by using fast Fourier transform (FFT). The user can set any power exponent of 2 between 128 and 4096 for the number of digital signals (data) to be supplied to FFT.

While a LAN interface is used as the interface between the instrument 9 and the personal computer 10 in Embodiment 1, any other standard interface such as RS-232C, GP-IB, and USB may be used instead. In addition to the signals, temperature in the sample room set by the personal computer 10, pressure of the force of pushing the syringe, time, electrophoresis voltage, and sample number to be analyzed are transferred to the central processing unit 53 via the LAN interface.

The central processing unit 53 controls the automatic translation stage 28, automatic rotation stage 40, and automatic z-stage 41 via the motor controller 55 and power to be input to the heater 47 via the temperature controller 56. The motor controller 55 controls the moving speed of the automatic translation stage 28, based on the output of the pressure sensor 27. The temperature controller 56 controls power to be input to the heater 47, based on the resistance value of the temperature sensor 48.

Via the digital output, the central processing unit 53 also exerts on/off control of the power supply 3 of high voltage, open/close control of the buffer tank 37 operated by solenoid 39, on/off control of the power supply 59 for the light source 15. Moreover, the central processing unit 53 controls output voltage of the power supply 3 of high voltage via the low-voltage analog output 57.

Figure 8:
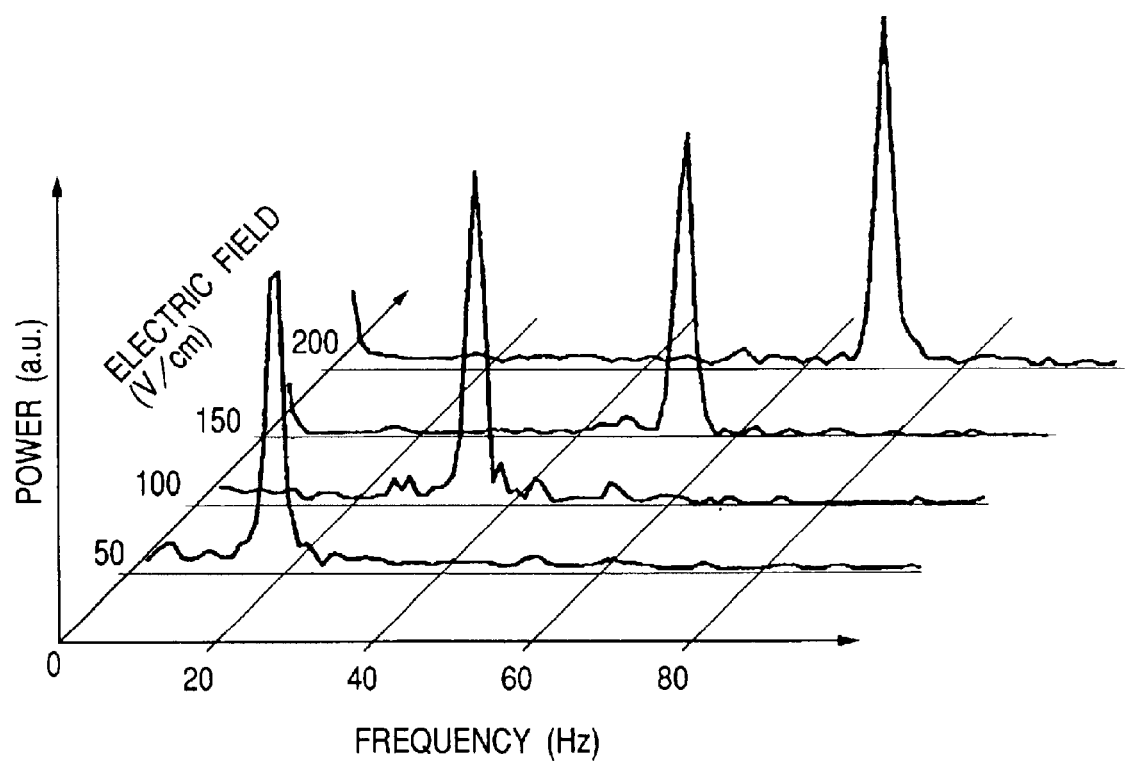
FIG. 8 shows an exemplary result of analyzing a λ-DNA sample labeled with TOTO-1 in Embodiment 1 of the present invention.

FIG. 8 shows an exemplary result of actual analysis of a DNA sample carried out by Embodiment 1. This drawing represents the power spectrum of fluctuation of fluorescence detected by electrophoresis with application of four voltages 50, 100, 150, and 200 V/cm, using the same analyte sample and TBE as the sieving matrix that is the same solution as the buffer for electrophoresis. Conditions other than the electrophoresis voltage are common; pitch of interference fringes p=10 $\mu$m, temperature is 30° C., the number of signals (data) collected for execution of FFT is 256, detection time is about one second. Data collection was performed as follows. After sample injection starts with application of 50 V/cm, about two minutes are allowed for the analytes to disperse across the detection region (length L=1 mm in the migration direction) in the capillary and data collection is performed. Then, the electrophoresis voltage is changed to 100, 150, and 200 V/cm and data collection is performed for about one second with application of each voltage.

The sample analyte is double-stranded $\lambda$-DNA with base length of 48000 bp onto which fluorescent dye TOTO-1 is coupled. Adjustment is made by mixing 10 $\mu$l of a dimethyl sufoxide (DSO) solution containing TOTO-1 of 0.1 $\mu$M concentration and 150 μl of a TBE solution containing λ-DNA of 500 ng/ml concentration. The fluorescent dye TOTO-1 is a dimer of thiazole orange inductor put on the market by Molecular Probes, Inc. The TOTO-1 is coupled onto the double-stranded DNA at a proportion of one molecule to 20 to 30 bases and its absorption peak is 514 nm and fluorescence peak is 533 nm.

The center frequencies of the spectrum peaks shown in FIG. 8 are 17 Hz, 33 Hz, 52 Hz, and 68 Hz and corresponding migration velocity of analyte is 0.17 mm/s, 0.33 mm/s, 0.52 mm/s, and 0.68 mm/s, respectively, which is substantially proportional to the electrophoresis voltage. The mobility of λ-DNA in the TBE obtained from the above results is $3.4 \times 10^{-8}$ $m^2V^{-1}s^{-1}$ which well agrees with the velocity of migration, about $3.5 \times 10^{-8}$ $m^2V^{-1}s^{-1}$ obtained from FIG. 3 which was provided in prior art-2.

Figure 9:
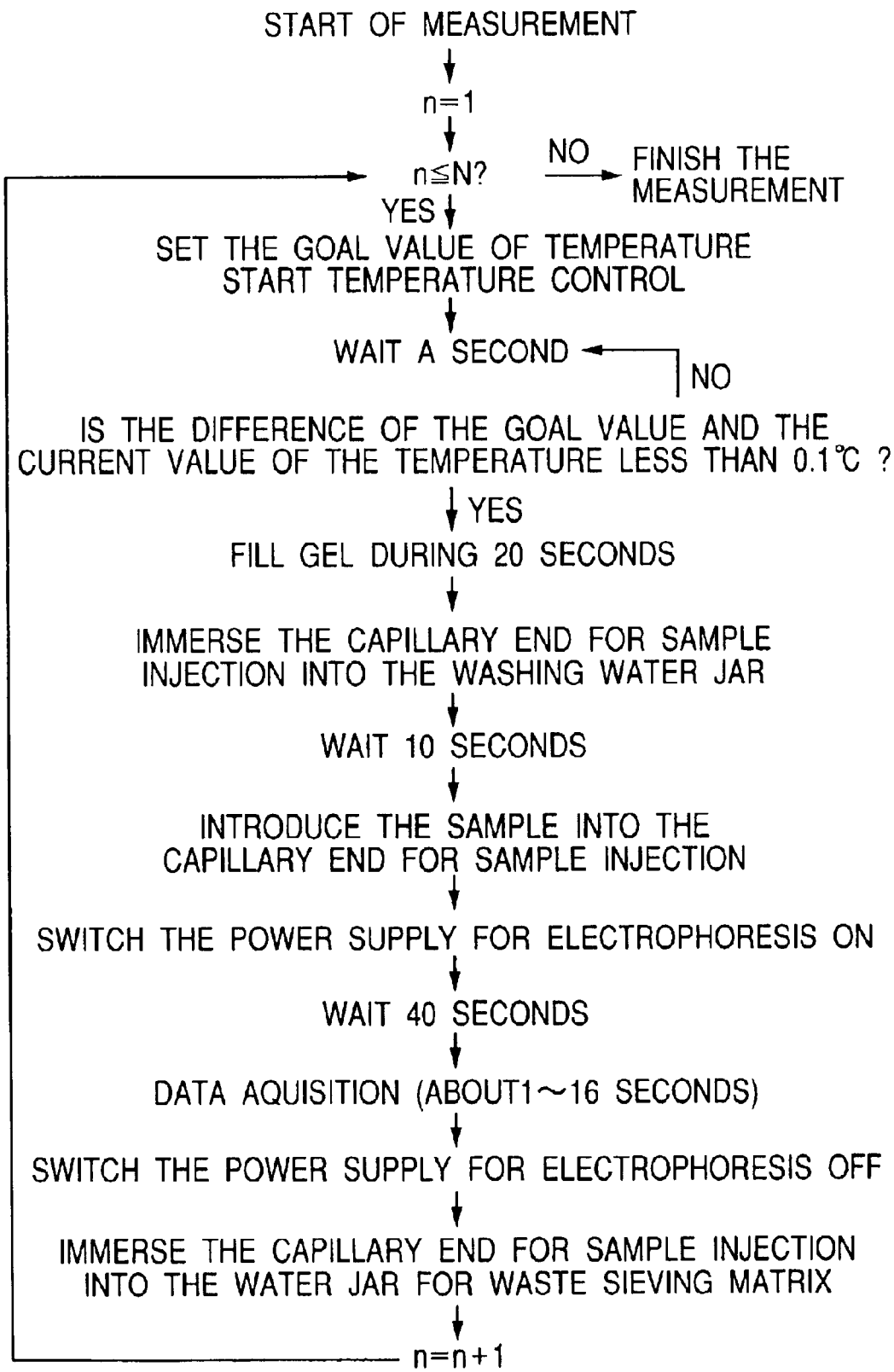
FIG. 9 is a flowchart of a procedure for analyzing a plurality of different samples by continues automatic operation of the instrument of Embodiment 1 of the present invention.

FIG. 9 is a flowchart of a procedure for analyzing a plurality of different samples by continues automatic operation of the instrument of Embodiment 1.

For the electrophoresis analysis illustrated by this flowchart, the following are assumed: 3% polyacrylamide TBE solution is used as the sieving matrix; electrophoresis voltage is 200 V/cm; temperature is 30° C.; and DNA dyed with TOTO-1 of 100 bp to 1000 bp is analyzed. Under these conditions, because the velocity of DNA migration falls within a range of 0.26 to 0.45 mm/s, it is sufficient to allow 40 seconds for the sample coming to the detection point (region) from the injection start point. N pieces of samples are analyzed; sample 1, 2, . . . , N.

When the power supply is turned on, in the initial state of the instrument, the sample injection end of the capillary is immersed in the water jar for waste sieving matrix 61. Measurement will always start from this state. By comparing parameter n that is initialized to a value of 1 when measurement starts with N to see which is greater, it is determined whether samples to be measured still remains. If no samples remain, the measurement process terminates. If samples to be measured remain, temperature control starts to adjust the temperature to the target of the set temperature. If the current temperature and the target temperature match with accuracy to ±0.1° C., charging with gel is performed for 20 seconds. Then, immerse the sample injection end of the capillary in the washing water jar 60 for 10 seconds. After washing the sample injection end of the capillary, injecting sample analytes to be measured in succession starts. 40 seconds after, data collection starts and continues for a time until the set number of signals (data) have been collected.

Upon the completion of data collection, the power supply for electrophoresis is turned off and the sample injection end of the capillary returns to the water jar for waste sieving matrix 61. Then, n=n+1 is set and the process proceeds to the next measurement cycle. In Embodiment 1, the water jar for waste sieving matrix and the washing water jar are separate and the protocol ensures that the sample injection end of the capillary is immersed in the water jar for waste sieving matrix 61 before being immersed in the washing water jar 60. This prevents the sample deposited to the tip of the capillary from entering the washing water jar 60, and, in effect, completely prevents carry over during the continuous measurement of samples.

Estimating the diffusion coefficient D of DNA of 100 to 1000 bp to be the order of $10^{-11}$ $m^2/s$ substantially, and using this estimate and L=1 mm and V=0.3 m/s, $p_O=18$ μm is obtained from mathematical expression 1. When analyzing DNA that falls within the range of 100 to 1000 bp, p=20 um is set. When analyzing other samples, p should be set, according to mathematical expression 20 to which the migration velocity and diffusion coefficient of the sample to be analyzed must be assigned.

Under the conditions for Embodiment 1 (L=1 mm, p=20 um, and $p_O=18$ μm), the number of theoretical plates (NTP)= 2810 is obtained from mathematical expression 11. Substantially complete separation of two species of analytes for which average mobility is $\mu_{AV}$ and mobility difference is $\Delta\mu$ is achieved, subject to constraint $\Delta\mu/\mu_{AV} \geq 0.113$.

FIG. 10 shows power spectrum diagrams obtained by analyzing double-stranded DNA analyte samples dyed with TOTO-1, which was performed using the protocol illustrated in FIG. 9 in the same manner as for measurement shown in FIG. 8. These power spectrum diagrams are exemplary results of numerical simulation using mathematical expressions 3 and 8. FIG. 10(A) shows an exemplary result of numerical simulation analyzing a mixture sample of DNA of 300 bp and DNA of 500 bp. FIG. 10(B) shows an exemplary result of numerical simulation analyzing a mixture sample of DNA of 400 bp and DNA of 500 bp. FIG. 10(C) shows an exemplary result of numerical simulation analyzing a mixture sample of DNA of 450 bp and DNA of 500 bp. FIG. 10(D) shows an exemplary result of numerical simulation analyzing a mixture sample of DNA of 490 bp and DNA of 500 bp. For the above analysis, it was assumed that, with application of electrophoresis voltage of 200 V/cm, the migration velocity of the DNAs of 300, 400, 450, 490, and 500 bps is 0.347, 0.323, 0.313, 0.305, and 0.303 mm/s, respectively. It was also assumed that L=1 mm, p=20 um, $p_O=18$ μm, and $D=1 \times 10^{-11}$ $m^2/s$.

Figure 10A:
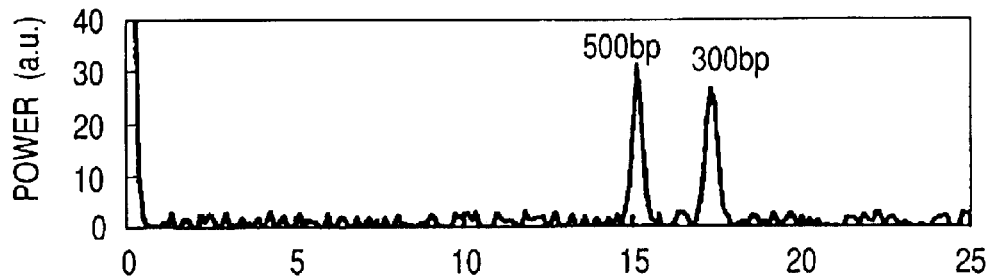
FIG. 10 shows (A) an exemplary result of numerical simulation analyzing a mixture sample of DNA of 300 bp and DNA of 500 bp, (B) an exemplary result of numerical simulation analyzing a mixture sample of DNA of 400 bp and DNA of 500 bp, (C) an exemplary result of numerical simulation analyzing a mixture sample of DNA of 450 bp and DNA of 500 bp, and (D) an exemplary result of numerical simulation analyzing a mixture sample of DNA of 490 bp and DNA of 500 bp.
Figure 10B:
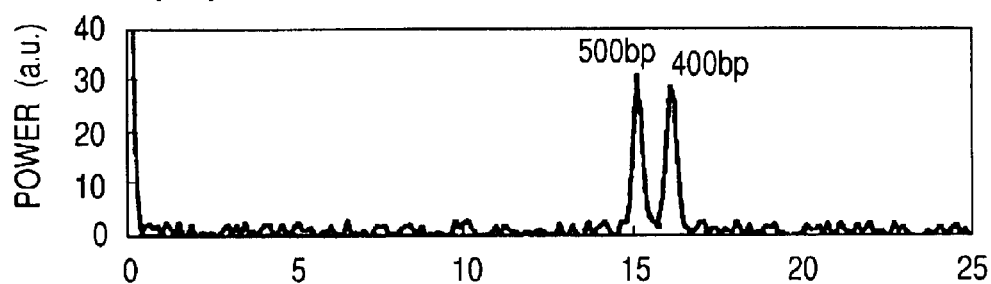
Figure 10C:
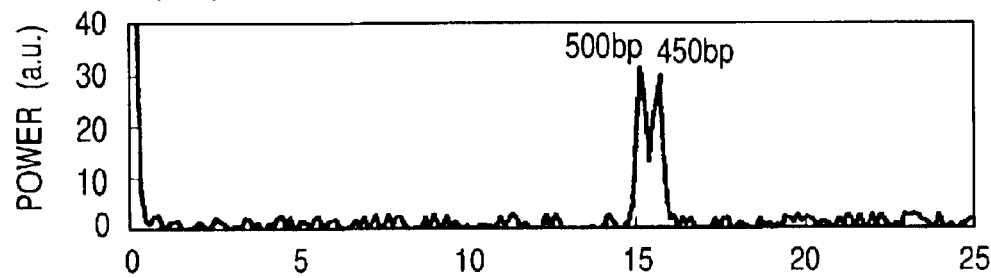
Figure 10D:
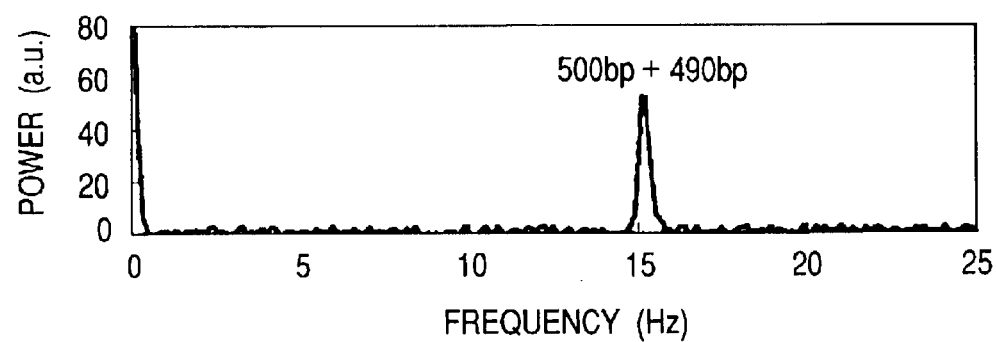

In the exemplary result shown in FIG. 10(A), $\Delta\mu/\mu_{AV}=$ 0.135, the base board between two peaks is as low as the noise level, and the peaks are completely separated enough to make their entire waveforms distinguishable. In the exemplary result shown in FIG. 10(B), $\Delta\mu/\mu_{AV}=0.064$, the waveforms of two peaks slightly overlap at the base board between them, and their entire waveforms are not completely separated in a ideal view. In the exemplary result shown in FIG. 10(C), $\Delta\mu/\mu_{AV}=0.032$, the waveforms of two peaks overlap at the base board between them, and their entire waveforms are not separated though the peaks are detected separately in position. In the exemplary result shown in FIG. 10(D), $\Delta\mu/\mu_{AV}=0.007$, the waveforms of two peaks overlap entirely and are not separated.

The power spectrum diagrams shown in FIG. 10 are those directly displayed from the power spectrum for each sample obtained through predefined calculation from 4096 signals (data) collected during about eight seconds. Although noise appears, SNR can be enhanced by repeating data collection and calculation of power spectrum and integration.

While TOTO-1 is used as fluorescent dye for labeling analyte samples in Embodiment 1, essentially the same analysis can be performed, using YOYO-1 (put on the market by Molecular Probes, Inc.) instead. Because YOYO-1 is characterized in that the number of molecules coupled onto DNA is more than TOTO-1, higher SNR can be attained with YOYO-1. By replacement of the light source 15 and the filter 43, other dyes such as, for example, rhodamine dye can be used suitably. Instead of staining the samples with a dimer beforehand, it may be preferable to allow monomer dye such as TO-PRO-1 and YO-PRO-1 (put on the market by Molecular Probes, Inc.) to disperse in the migration channel and couple onto unlabeled DNA injected into the channel.

Embodiment 2

Figure 11:
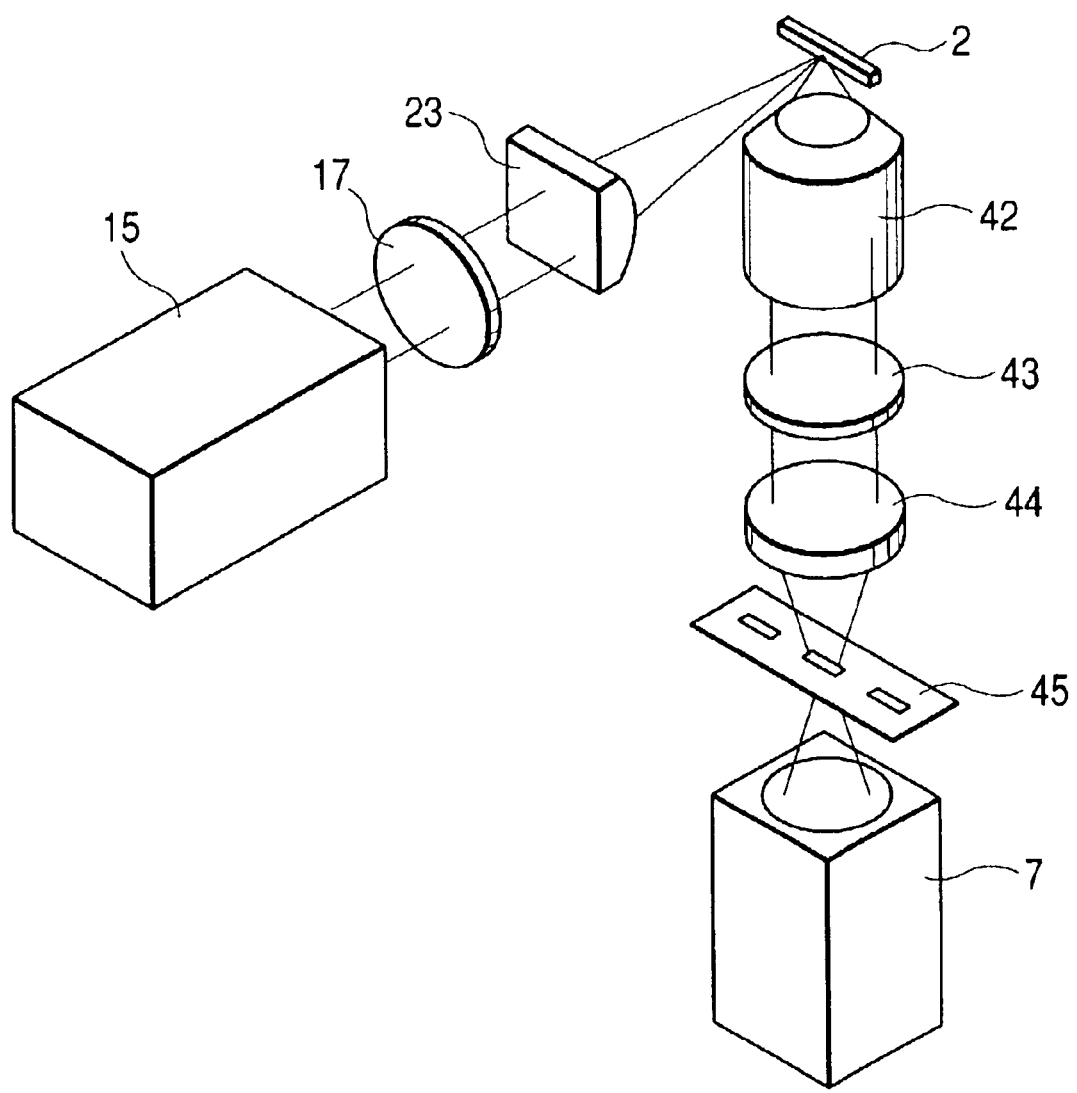
FIG. 11 shows the configuration of the primary part of an instrument for florescence detection embodied as a preferred Embodiment 2 of the present invention.

FIG. 11 shows the configuration of the primary part of an instrument for florescence detection embodied as a preferred Embodiment 2 of the present invention. The components of the instrument of Embodiment 2 differ from the instrument of Embodiment 1 in that the optical interferometer is not used and the slit 45 structure. In Embodiment 2, from the argon ion laser (light source 15) capable of generating light with wavelength of 488 nm and output of 10 mW, excitation light radiates horizontally as collimated beams having a circular section with a diameter of 1 mm (diameter of $e^{-2}$). After passing through the filter 17, the vertical diameter of the excitation light is narrowed to 50 µm by the cylindrical lens 23 and the excitation light is applied to the migration channel 2 formed within the horizontally located capillary of square quarts. The dimensions of the capillary (migration channel) are the same as those of the migration channel of the instrument of Embodiment 1. Fluorescence emission from the analytes in the migration channel is detected by detection optics consisting of a lens 42, filter 43, lens 44, slit 45, and detector 7. The structure of the detection optics is essentially the same as for the instrument of Embodiment 1 except that the optical axis is vertical and the light travels downward vertically. The optics makes a real image of the detection region magnified by 20 times and converges the image on a hole position of the slit 45 plate.

Figure 12:
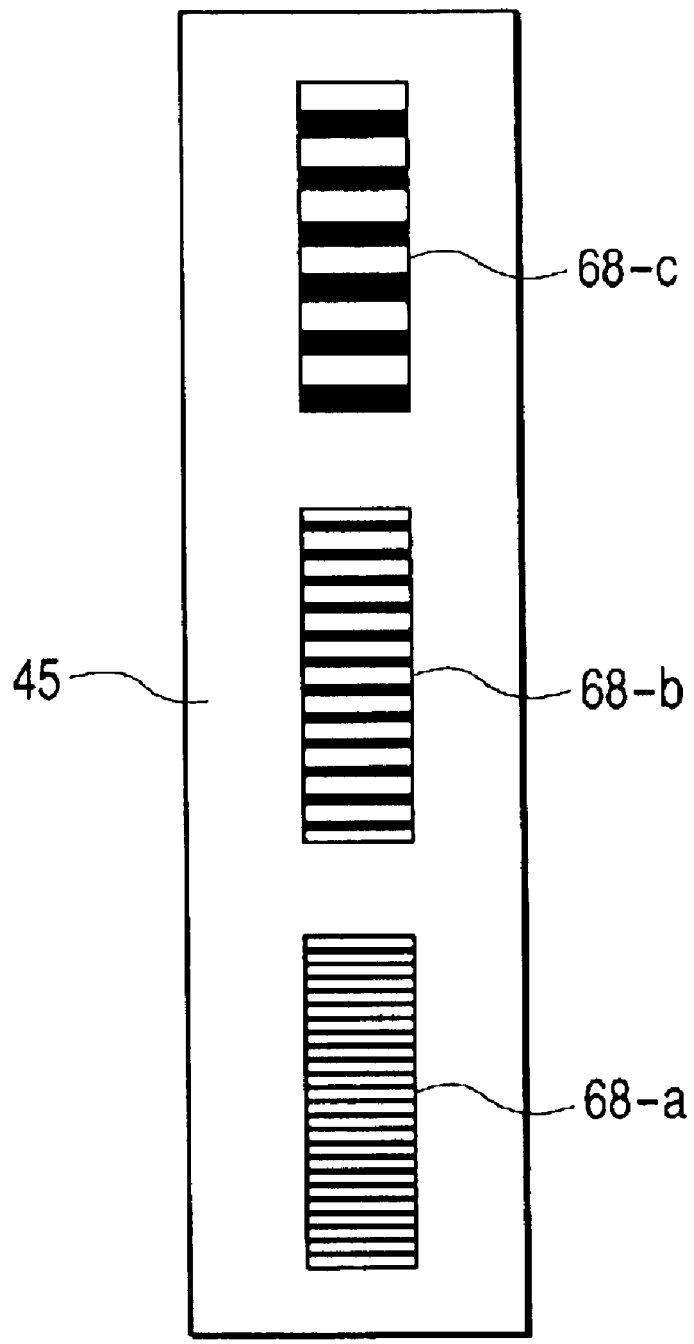
FIG. 12 shows an enlarged view of a slit used in the instrument of Embodiment 2 of the present invention.

FIG. 12 shows an enlarged view of the slit 45 used in the instrument of Embodiment 2. The slit 45 is a metal plate with three rectangular holes and its surface is black coated. In the rectangular holes, substrates 68-a, 68-b, and 68-c are fit, respectively. Transmittancy of each substrate periodically changes in the direction that the analytes move, according to a sine wave or square wave function. A substrate on which the real image of the detection region is converged can be optionally selected from the three substrates by sliding the slit longitudinally.

Pitch p by which the transmittancy of the substrates 68-a, 68-b, and 68-c periodically changes is 0.2 mm, 0.4 mm, and 0.8 mm, respectively. The exemplary substrates 68-a, 68-b, and 68-c shown in FIG. 12 have a formation of 100, 50, and 25 pairs of a great transmittancy step (white) and a small transmittancy step (black), respectively.

Because the image made on one of the substrates is magnified by 20 times, locating the substrates at the position of the image is substantially equivalent to assigning p=10 µm, p=20 µm, and p=40 µm, respectively, to mathematical expression 4. Samples to be analyzed in Embodiment 2 are a solution of mixture samples of DNA of 300 bp and DNA of 500 bp, mixture samples of DNA of 400 bp and DNA of 500 bp, mixture samples of DNA of 450 bp and DNA of 500 bp, and mixture samples of DNA of 490 bp and DNA of 500 bp, which are used in Embodiment 1. Thus, by selecting p=20 µm and processing the outputs of the detector 7 in the same way as in Embodiment 1, the same result can be obtained as in Embodiment 1. More generally, when the magnifying power of the image made on the slit 45 is represented by M, mathematical expression 20 can be rewritten to mathematical expression 39.

Mathematical Expression 39

$$p/M \sim p_0 \quad \text{[Mathematical expression 39]}$$

Because the instrument of Embodiment 2 does not employ the optical interferometer in the optics for applying the excitation light to the detection region, its advantage is robustness against vibration and shock and, consequently, it can be made portable. Pitch p can be changed readily by sliding the slit 45 and adjusting the inching stages is not necessary. Embodiment 2 is preferable for a case where the diffusion coefficient of sample analytes is unknown and selecting from a plurality of pitches p must be done when executing analysis.

Figure 13:
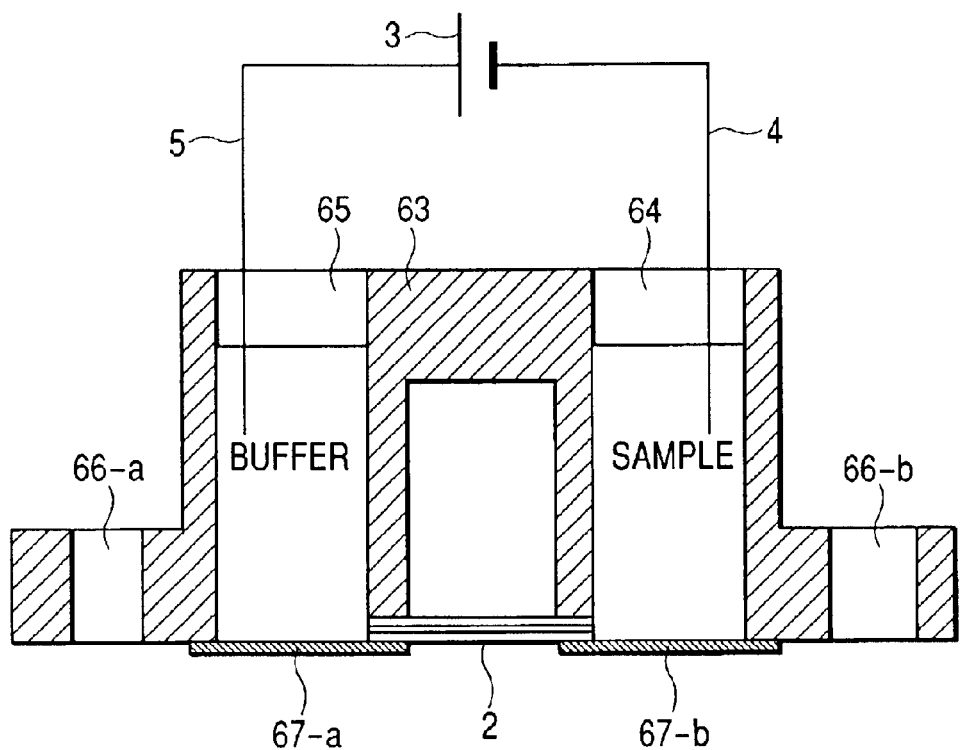
FIG. 13 shows an enlarged sectional view of a vertical plane containing a migration channel and its periphery of the instrument for fluorescence detection of Embodiment 2 of the present invention.
Figure 14:
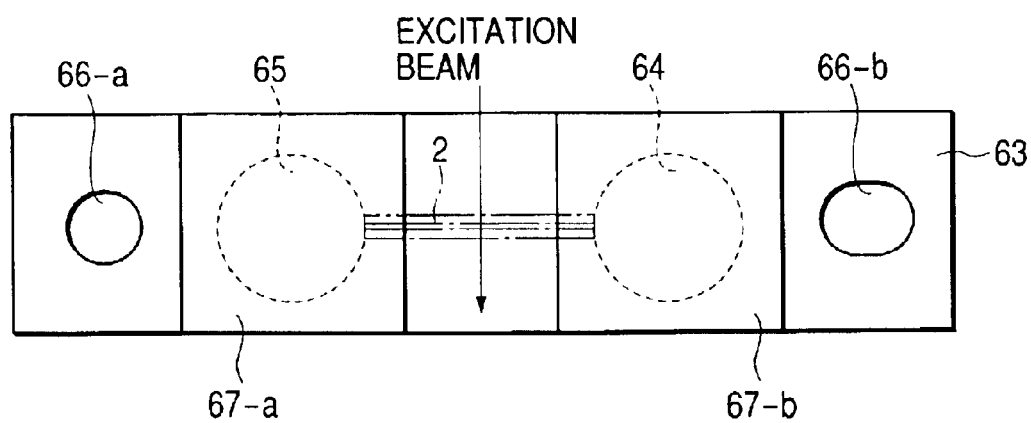
FIG. 14 shows a bottom plan view of the migration channel and its periphery shown in FIG. 13.

FIG. 13 shows an enlarged sectional view of a vertical plane containing the migration channel 2 and its periphery of the instrument for fluorescence detection of Embodiment 2. FIG. 14 shows a bottom plan view of the migration channel and its periphery shown in FIG. 13. The migration channel 2 made of the capillary is fit in a transparent polycarbonate holder 63 and sandwiched between a sample well 64 and a buffer well 65 hollowed in the holder on its either side. The bottoms of the sample well 64 and the buffer well 65 are closed by 0.1-mm thick stainless bottom plates 67-1 and 67-b, respectively.

The mutual contact surfaces of the holder 63, migration channel 2, and bottom plates 67-a and 67-b are sealed by bond. Holes 66-a and 66-b are bolt holes for securing the holder to the detection optics. First, the buffer well and the migration channel 2 are charged with the sieving matrix that also servers as the buffer solution for electrophoresis by the force of the syringe. After a sample solution is pipetted with a micro pipet into the sample well 64, electrophoresis by the electrodes 4 and 5 takes place.

The entire length of the capillary is 6 mm in Embodiment 2 and the detection region in the center of the capillary is 1 mm wide. Distance of migration required until analytes disperse across the detection region is only 3.5 mm. This is advantageous because of shorter wait time. If, for example, analytes to migrate at velocity of 0.3–0.4 mm/s are detected, after the start of migration, only a short time of about 10 seconds is allowed to pass before data collection starts. Because the entire length of the migration channel is as short as 6 mm, for example, when a slope of potential of 200 V/cm takes place, potential difference across the channel is only 120 V. High voltage of power supply, 10 kV or above, which would be required for conventional electrophoresis is not necessary. Thus, it is unnecessary to take insulation measures against high voltage.

Because fluorescence is detected from under the structure shown in FIG. 13, a lens of high lightness and a short operating distance can be used. Thus, higher sensitivity than Embodiment 1 can be attained by the instrument of Embodiment 2. In Embodiment 2, as the lens 42, an object lens with a numerical aperture of 0.75 and operating distance of 0.61 mm is used.

In Embodiment 2, the structure of the holder 63 and the migration channel 2, shown in FIG. 13, is disposable. Thus, unintended contamination with a different sample does not take place and a risk of contamination with suspended particles in the air can be reduced lower than when the migration channel is used repeatedly. Embodiment 2 makes it possible to safely analyze even substances such as RNA and proteins that are liable to react to enzymes and more unstable than DNA.

Embodiment 3

Figure 15:
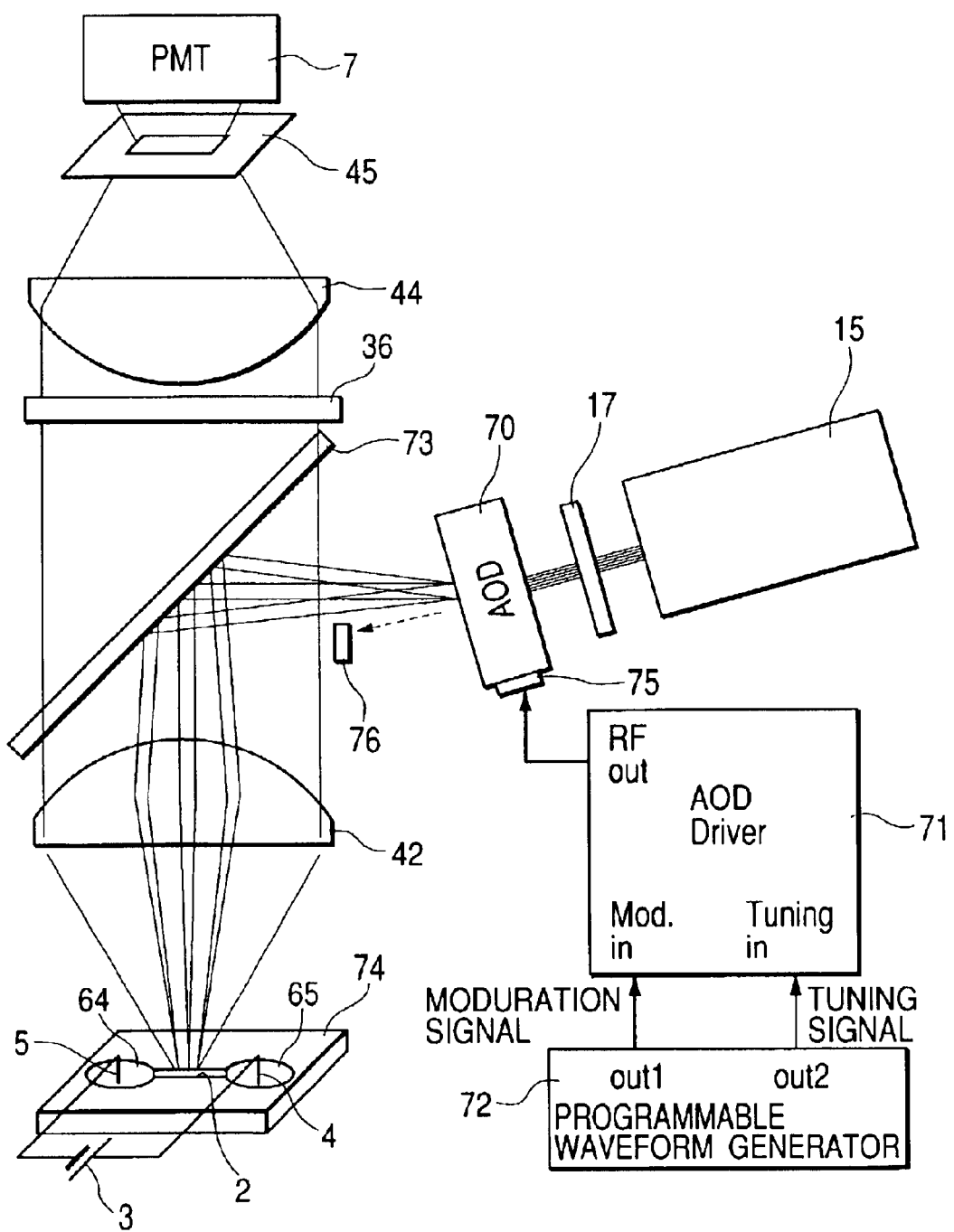
FIG. 15 shows the configuration of the primary part of an instrument for florescence detection embodied as a preferred Embodiment 3 of the present invention.

FIG. 15 shows the configuration of the primary part of an instrument for florescence detection embodied as a preferred Embodiment 3 of the present invention. In Embodiment 3, the excitation light is applied to the detection region of the migration channel and a beam spot is scanned at high speed with blinking light beams. The excitation light is controlled to have an intensity profile that periodically changes, according to a sine wave or square wave function. As the light source 15, a second harmonic laser of neodymium-yttrium-garnet(Nd-YAG) is used which is capable of outputting Gaussian beams with wavelength $\lambda$=532 nm, output of 10 mW, and a beam diameter of 3 mm.

Beams radiated from the light source are allowed to pass through the filer 17 with center wavelength of 532 nm and half width of 10 nm. After spectrum purity is thus enhanced, the beams are input to an acoust-optic deflector (AOD) 70. The AOD 70 is a molybdenous oxychloride monocrystal structure to which an acoustic transducer 75 is attached. The acoustic transducer 75 converts radio frequency (RF) signals input from an AOD driver 71 into ultrasonic (acoustic) waves. The ultrasonic (acoustic) waves are transmitted across the AOD 70.

The beams input to the AOD 70 are diffracted by the ultrasonic (acoustic) waves and change their direction to travel, according to the RF signal frequency. In FIG. 13, transmitted light not diffracted by the AOD 70 is denoted by a dash line and diffracted light is denoted by a solid line. When RF signal output is off, light input to the AOD 70 is transmitted without being diffracted and output as transmitted light that is absorbed by a beam stop 76. A relation between RF signal frequency ν and diffraction angle θ is expressed by mathematical expression 40, where $c_s$ is sound speed within the AOD. In Embodiment 3, $c_s$=3630 m/s.

Mathematical Expression 40

$$\theta=2\sin^{-1}\{\lambda\nu/(2c_s)\}$$ [Mathematical expression 40]

The AOD driver 71 has two input pins for modulation signal and tuning signal in addition to the RF signal output pin. RF signal amplitude is between 0 and the maximum output in proportion to the modulation signal VM that falls within a range of 0 to 1 V. Diffracted light intensity is proportional to the RF signal amplitude and thus it is proportional to the modulation signal. A relation between RF signal frequency ν and tuning signal $V_T$ [V] that falls within a range of 2 to 12 V is expressed by mathematical expression 41. Modulation can be performed in a range of 60 to 100 MHz.

Mathematical Expression 41

$$\nu=4(V_T-2)+60 [\text{MHz}]$$ [Mathematical expression 41]

Output out1 from a programmable waveform generator 72 is input to the modulation signal input of the AOD driver 71 and output out2 from the programmable waveform generator 72 is input to the tuning signal input of the AOD driver 71. From the out1 pin, sine waves for which the minimum value is 0 V and the maximum value is 1 V are output. From the out2 pin, saw-tooth waves for which the minimum value is 2 V and the maximum value is 12 V are output. The out1 and out2 signals are generated from a common reference clock signal of 200 MHz that is internally provided in the programmable waveform generator. Thus, setting an exactly integral ratio of output signal frequency to clock frequency and complete phase synchronization can be achieved.

The light diffracted by the AOD 70 is reflected by a dichloic mirror 73 that reflects light with wavelength of 550 nm or shorter and allows light with wavelength longer than 550 nm to pass, narrowed to a diameter of 20 μm by a lens 42, and applied to the center of the migration channel 2 engraved on the quarts substrate 74.

The length of the migration channel 2 in the migration direction is 1.5 mm and its section intersecting the migration direction orthogonally is a square of 50 μm in both width and depth. The lens 42 is a camera lens having lightness of 0.95 and focus distance f=105 mm. The optical axis of the lens 42 is set aligned with the optical axis of the light diffracted by the AOD 70 when an average of RF signal frequency output from the AOD driver 71, $\nu_m$=80 MHz.

On the quarts substrate 74, a sample well 64 and a buffer well 65 are provided at either end of the migration channel 2. Using a micro pipet, fill the buffer well 65 and the migration channel 2 with a sieving matrix and the sample well with a sample solution. When voltage from the power supply 3 is applied to the line between the electrode 5 located in the sample well and the electrode 4 located in the buffer well, electrophoresis of the analytes takes place.

Because the length of the migration channel in Embodiment 3 is 1.5 mm, even when a voltage of 200 V/cm is applied, the required power supply voltage is only 30 V. A power supply for weak power use is sufficient and it is unnecessary to take insulation measures against high voltage.

Fluorescence emission from the analytes is collected by a lens 42 and formed into collimated beams which then pass through the dichloic mirror 73 and a filter 44 with center wavelength of 570 nm and half width of 40 nm. The beams are converged by a lens 44 on the slit 45 and an image is made on the slit and detected by the detector 7.

The instrument of Embodiment 3 can be suitably applied to analyzing samples labeled with POPO-3 (put on the market by Molecular Probes, Inc.) or the like. In Embodiment 3, the focus distance of the lens 44 is set at 210 mm, an imaging system of double magnifying power is configured, and the slit 45 is 50 μm wide.

The outputs from the detector 7 are processed in exactly the same way as in Embodiment 1 and sampling is performed with a sampling frequency of 250 Hz. Under the conditions of Embodiment 3, mathematical expression 40 can be rewritten to $\theta=\lambda\nu/c_s$ by approximation. Thus, displacement δ from the beam spot center is expressed by mathematical expression 42. The beam spot is scanned in cycles of the tuning signal frequency with the beams blinking in cycles of the modulation signal frequency.

Mathematical Expression 42

$$\delta=f\lambda(\nu-\nu_m)/c_s$$ [Mathematical expression 42]

If the tuning signal frequency is sufficiently high, the same effect as presumed through calculation by assigning L that is obtained by mathematical expression 43 and p that is obtained by mathematical expression 44 to mathematical expression 4 can be realized. In mathematical expression 43, $\nu_{MAX}$ is the maximum RF signal frequency and $\nu_{MIN}$ is the minimum RF signal frequency. In Embodiment 3, $\nu_{MAX}$=100 MHz and $\nu_{MIN}$=60 MHz. m denotes a ratio of modulation signal frequency to tuning signal frequency. In Embodiment 3, the tuning signal frequency is set at 10 kHz, which is sufficiently high as compared with the sampling frequency of 250 Hz at which the outputs from the detector are sampled. When the above values applied in Embodiment 3 are assigned to mathematical expression 43, L=0.59 mm is obtained.

Figure 16:
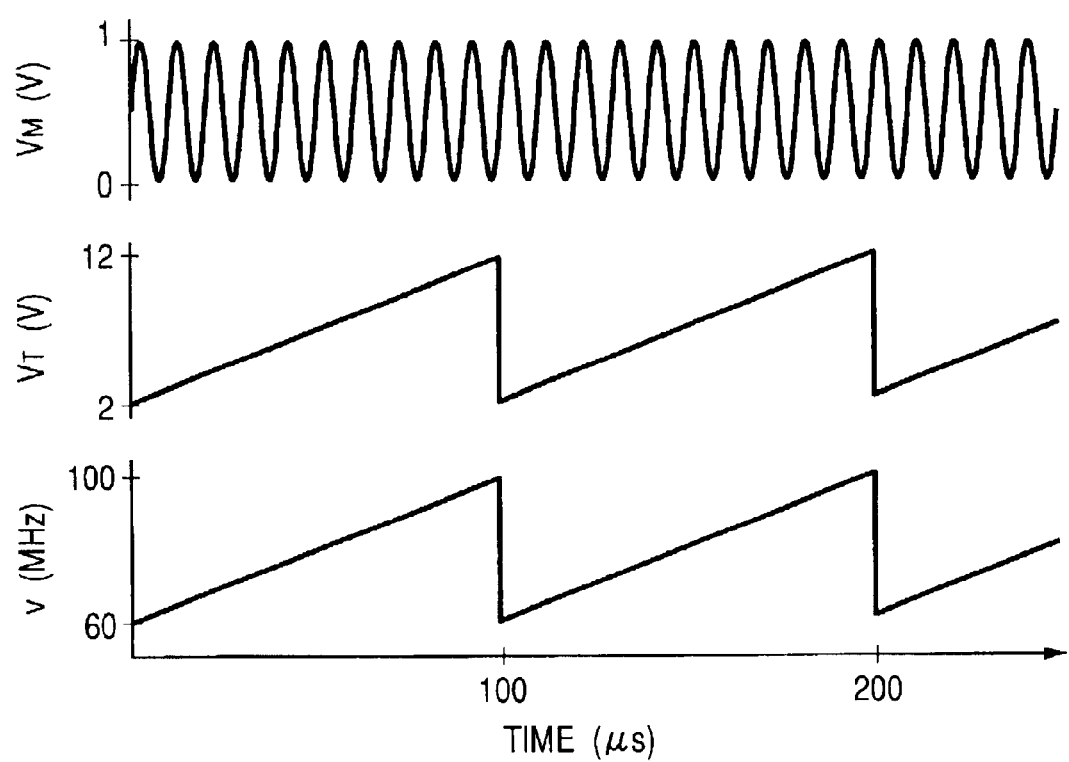
FIG. 16 shows a timing chart of modulation signal, tuning signal, and RF signal frequency in Embodiment 3 of the present invention.

FIG. 16 shows a timing chart of modulation signal, tuning signal, and RF signal frequency when m=10, assuming p=59 μm.

Mathematical Expression 43

$$L=f\lambda(\nu_{MAX}-\nu_{MIN})/c_s$$ [Mathematical expression 43]

Mathematical Expression 44

$$p=L/m$$ [Mathematical expression 44]

In Embodiment 3, a common lens is used for applying the excitation light to the detection region and collecting fluorescence and its advantage is the reduced number of lenses and optics to be adjusted. As is the case in Embodiment 2, the instrument of Embodiment 3 does not employ the optical interferometer in the optics and therefore is robust against vibration and shock and suitable for outdoor use. Changing pitch p of excitation light intensity profile can be carried out by electrically without using a mechanically movable part. Embodiment 3 is suitable for automatic data collection and measurement for the same sample while selecting from among multiple p values.

While the acoust-optic deflector is used for scanning the beam spot while changing the direction in which the excitation light travels in Embodiment 3, it may be preferable to use a Galvano mirror instead. While, in Embodiment 3, the intensity of the laser beam is modulated to periodically change, according to a sine wave function, it may be preferable to turn the intensity high and low periodically, according to a square wave function, scan the detection region at high speed, and apply the excitation light controlled to have an intensity profile that periodically changes to the detection region.

In further preferred embodiments which will be described hereinafter, the excitation light of constant intensity is applied to the detection region instead of the excitation light controlled to have an intensity profile that periodically changes. Using a one-dimensional or two-dimensional optical detector, fluorescence emission from the analytes is detected and a power spectrum of the detected fluorescence is obtained through calculation by an arithmetic unit.

Embodiment 4

Figure 17:
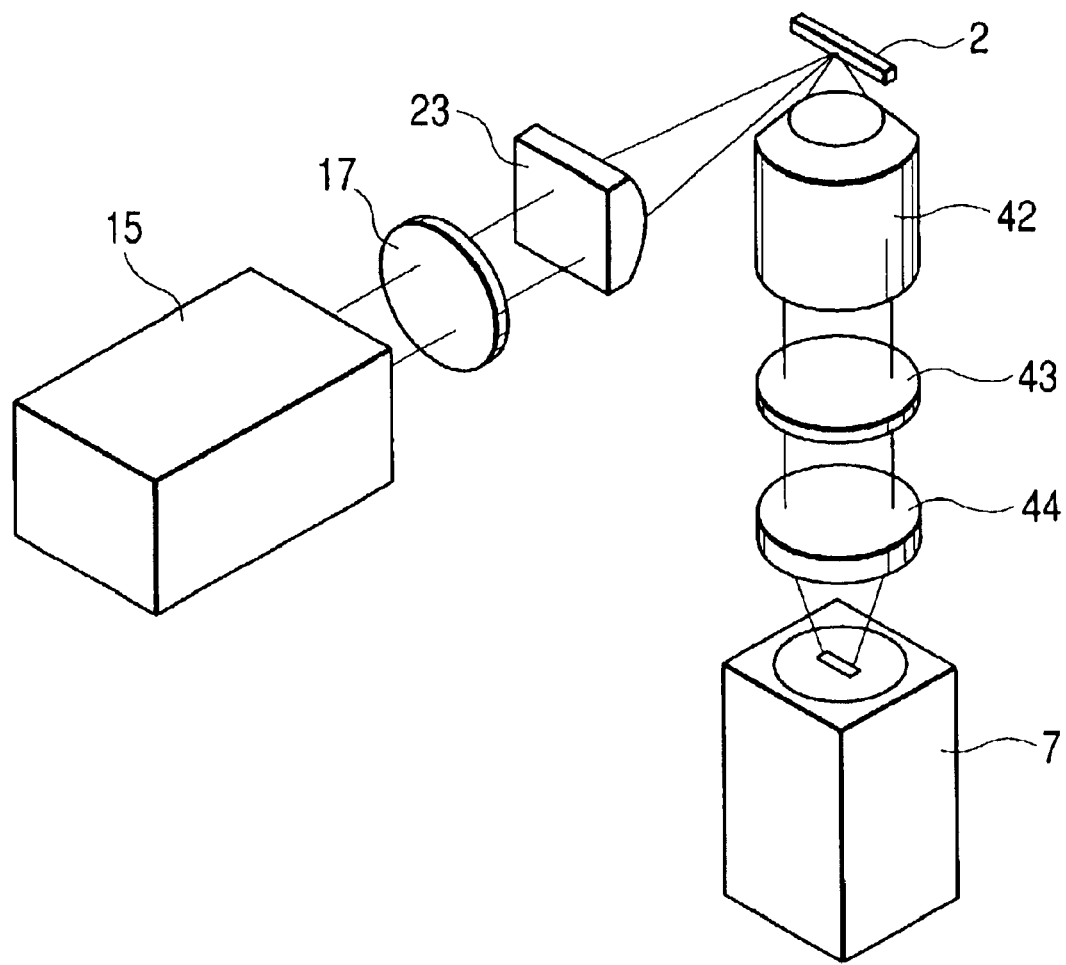
FIG. 17 shows the configuration of the primary part of an instrument for florescence detection embodied as a preferred Embodiment 4 of the present invention.

FIG. 17 shows the configuration of the primary part of an instrument for florescence detection embodied as a preferred Embodiment 4 of the present invention. The configuration of the instrument of Embodiment 4 resembles that of Embodiment 2. That is, the instrument includes the same optics for applying excitation light from the light source 15 to the migration channel 2 and converging fluorescence emission from the analytes by the lens 44, thus making an image. The instrument of Embodiment 4 does not employ the slit used in Embodiment 2 and employs a one-dimensional image sensor as the detector 7. The photoelectric elements of the image sensor are arranged in the same direction that electophoretically migrating analyte images move. The photoelectric area of the image sensor where the photoelectric elements are arranged is oriented so that the lens 44 will converge the image on it.

Figure 18:
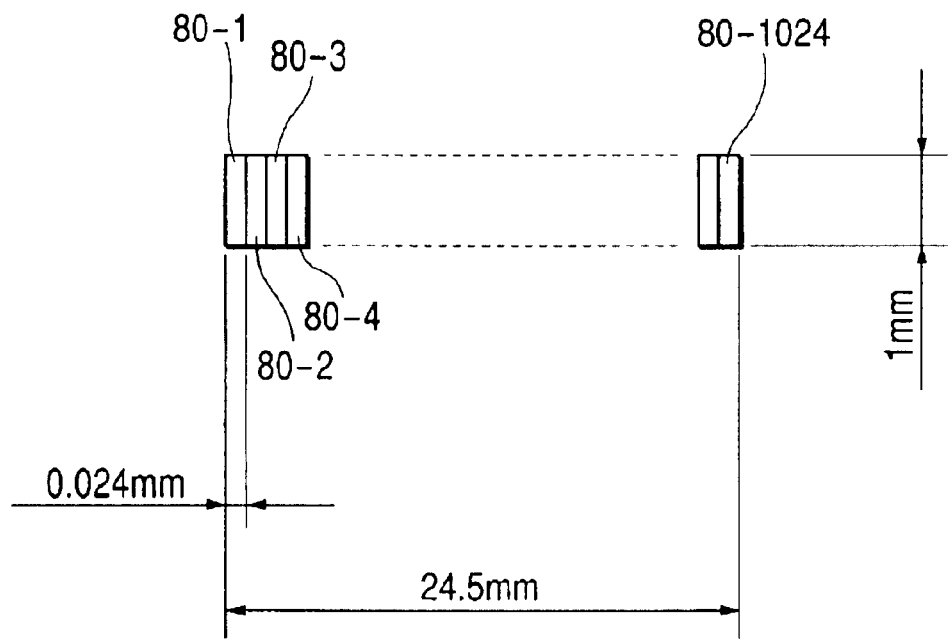
FIG. 18 shows an enlarged view of the photoelectric area of an image sensor used in Embodiment 4 of the present invention.

FIG. 18 shows an enlarged view of the photoelectric area of the image sensor used as the detector 7. The photoelectric area of 24.5 mm×1 mm is partitioned into 1024 photoelectric elements 80-1 to 80-1024. The dimensions of each photoelectric element are 0.024 mm×1 mm. The detector 7 repeats a cycle consisting of (1) exposure for 8 ms and (2) read for 2 ms reading charge quantity accumulated on each photoelectric element.

The thus read charge quantity is A-D converted and the resultant digital data thereof is transferred to the memory of the personal computer 10. Based on charge quantity $q_1$ to $q_{1024}$ accumulated on the photoelectric elements 80-1 to 80-1024, the microprocessor of the personal computer 10 evaluates mathematical expression 45 to obtain a value of q. Summation $\Sigma_i$ is calculated for i=1 to 1024. $p_2$ is pitch given by a pitch function and $k_2=2\pi/p_2$ is a constant to be determined, depending on the property of the solution including the sample. The value of q is approximately proportional to a value of i (t) obtained by assigning I (r) that is obtained by mathematical expression 46 to mathematical expression 1.

Mathematical Expression 45

$$q=\Sigma_i\{q_i \cos (k_2 i)\}$$ [Mathematical expression 45]

Mathematical Expression 46

$$I(r)=I_0\exp\{-8(x/L)^2\}\exp\{2\pi Mx/(p_1p_2)\}\times \exp\{-8(y/W)^2\}\exp\{-8(z/H)\}$$ [Mathematical Expression 46]

$p_1$ is pitch of intervals at which the photoelectric elements 80-1 to 80-1024 are arranged and M is magnifying power of an image to be made on the photoelectric area. In Embodiment 4, $p_1$=0.024 mm and M=20. L is width of excitation light beams hit on the migration channel 2 in the migration direction. H is width of excitation light beams hit on the migration channel 2 in the direction perpendicular to the migration direction. W is a value obtained by (length of photoelectric element in the direction intersecting the migration direction orthogonally)/(magnifying power M). In Embodiment 4, L=1 mm, H=0.05 mm, and W=0.05 mm.

By evaluating mathematical expression 45 and obtaining a value of q as the power spectrum, essentially the same result can be obtained by the instrument of Embodiment 4 as done in other embodiments. Advantage of Embodiment 4 is that, based on the data collected only once, evaluating mathematical expression 45, wherein the value of $k_2$ may vary, produces the same result as collecting data two or more times while changing the value of p in Embodiment 1. In Embodiment 4, $p_2$=16.7 μm is set to obtain the same effect as in the case where p=20 μm in Embodiment 1. More generally, mathematical expression 20 can be rewritten to mathematical expression 47.

Mathematical Expression 47

$$p_1p_2/M \neq p_0$$ [Mathematical expression 47]

Embodiment 5

In a preferred Embodiment 5 of the present invention, essentially the same structure as the optics for applying the excitation light to the detection region and detecting fluorescence used in Embodiment 4 and shown in FIG. 17 is applied, except that a two-dimensional image sensor is used as the detector 7. Structure resembling the structure of the migration channel and its periphery shown in Embodiments 2 and 4 is also used in Embodiment 5 wherein, however, a plurality of migration channels are assembled so that analytes of a plurality of species can be analyzed at the same time.

Figure 19:
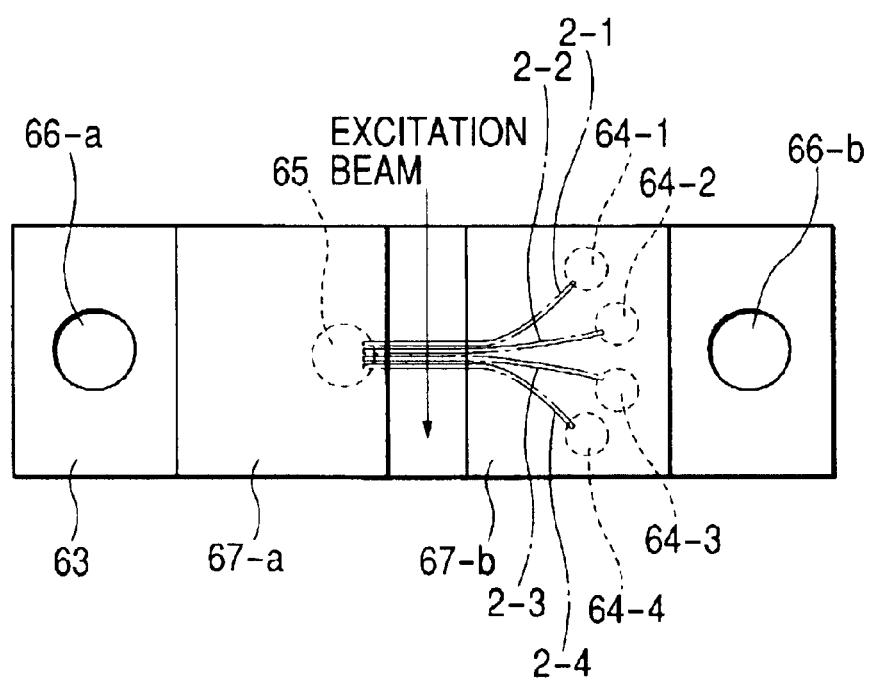
FIG. 19 shows an enlarged view of migration channels and periphery in a preferred Embodiment 5 of the present invention.

FIG. 19 shows an enlarged bottom plan view of migration channels and periphery in Embodiment 5; this view corresponds to the view shown in FIG. 14 in Embodiment 2. Migration channels 2-1 to 2-4 are quarts capillaries, each having a circular section with the outside diameter of 200 μm and the inside diameter of 50 μm. The capillaries 2-1 to 2-4 on one end branch in a sector, arranged at intervals of 0.24 mm pitch on the same plane on one side adjacent to a fluorescence detection point (detection region) irradiated by the excitation light. The capillaries 2-1 to 2-4 are oriented to be vertical to the excitation light in and near the detection region. The excitation light is applied to the detection region in the direction parallel to the plane adjacent to the detection region.

Excitation light beams passing through the capillary 2-1 is converged on the center of the migration channels 2-2, 2-3, and 2-4 in sequence by the lens effect of the capillary with its circular section. One-side ends of the capillaries 2-1 to 2-4 are connected to separate sample wells 64-1 to 64-4 respectively so that separate samples can be injected into them. The other-side ends of the capillaries 2-1 to 2-4 are connected to one common buffer well 65. One electrode for electrophoresis is located in each of the sample wells 64-1 to 64-4 and the other electrode for electrophoresis is located in the buffer well 65.

As the two-dimensional image sensor, a cooled CCD with 1024×1024 photoelectric elements arranged in a square is used. The photoelectric elements of the cooled CCD are arranged at intervals of 24 μm pitch in both the direction that the analytes move and the direction intersecting orthogonally the direction that the analytes move. Real images of the capillaries 2-1 to 2-4 in part (detection region) irradiated by excitation light are magnified by 20 times and converged on area where the photoelectric elements are arranged of the cooled CCD.

Charge quantity accumulated on a photoelectric element positioned in row i and column j is represented by $q_{ij}$ and $q_n$ that is given by mathematical expression 48 is calculated for cases n=1, 2, 3, 4, respectively. $\Sigma_j$ denotes summation for j=1 to 1024 and $\Sigma_i$ denotes summation for i=200 n+92 to 200n+131 (n 1, 2, 3, 4). As a result, for each migration channel 2-1 to 2-4, the same result is obtained as done through calculation of q by mathematical expression 45. By evaluating mathematical expression 48 and obtaining the power spectrum of value of $q_n$ for each channel, the samples supplied from the sample wells 64-1 to 64-4 can be analyzed at the same time.

Mathematical Expression 48

$$q_n = \Sigma_i \{\cos(k_2 j)\} \Sigma_i \{q_{ij}\}$$ [Mathematical expression 48]

In Embodiment 5, single excitation light generated from one common light source is applied to all migration channels at the same time, taking advantage of the lens effect of the migration channels. The power supply for electrophoresis is also common for all migration channels. In consequence, Embodiment 5 can realize throughput four times as much as Embodiment 4 with substantially the same cost for the components.

Embodiment 6

In Embodiment 6, the present invention is applied to quality evaluation of human genome DNA extracted from human blood, using the same instrument configuration as in Embodiment 1. To suitably use genome DNA as templates of polymerase chain reaction (PCR), it is ideal that genome DNA fragments disperse in length in the order of several tens of kbp or longer. However, due to turbulence during extracting DNA and freezing and defrosting during storage, genome DNA may be cut to length several kbps or shorter. Whenever performing PCR, it is desirable to make genome DNA quality evaluation.

Genome DNA evaluated in Embodiment 6 is extracted from human blood of 100 μl by complete blood count prepared as material by using a DNA extraction kit put on the market by Quiagen, according to the following protocol. Add 10 μl of protease K and 100 μl of Lysis buffer, supplied with the kit, to the 100 μl blood and stir the mixture. Incubate the mixture for 10 min. at 56° C. Add ethanol to the mixture and stir it. Transfer the reactive solution to an extraction column, subject it to centrifugal separation for one min., and discharge filtered solution. Then, repeat twice the steps of pouring 500 μl of washing solution in the extraction column and centrifugal separation for one min. Add an eluant of 70° C. to the column, incubate it for five min., subject it to centrifugal separation for one min., and take out genome DNA.

The sample analytes used in Embodiment 6 are TBE solution of genome DNA extracted from human blood by protocol and mixed TBE solution of 10-kbp, 48-kbp, and 97-kbp DNAs which is used as a molecular weight marker. The DNAs are dyed with the TOTO-1 fluorescent dye as is the case in Embodiment 1 and total DNA concentration is adjusted to 30 ng/ml.

In Embodiment 6, TBE solution of hydoroxypropylmethylcellulose of 0.25% concentration is used as a separation medium, electrophoresis voltage is 50 V/cm, and length of observation region L=1 mm. Under these conditions, the velocity of double-stranded DNA migration V=0.15 to 0.3 mm/s and translational diffusion coefficient $D \neq 10^{-12}$ m$^2$/s. Because of $p_0$=7.6 to 10.7 μm obtained from mathematical expression 10, p=10 μm was set in Embodiment 6.

Figure 20A:
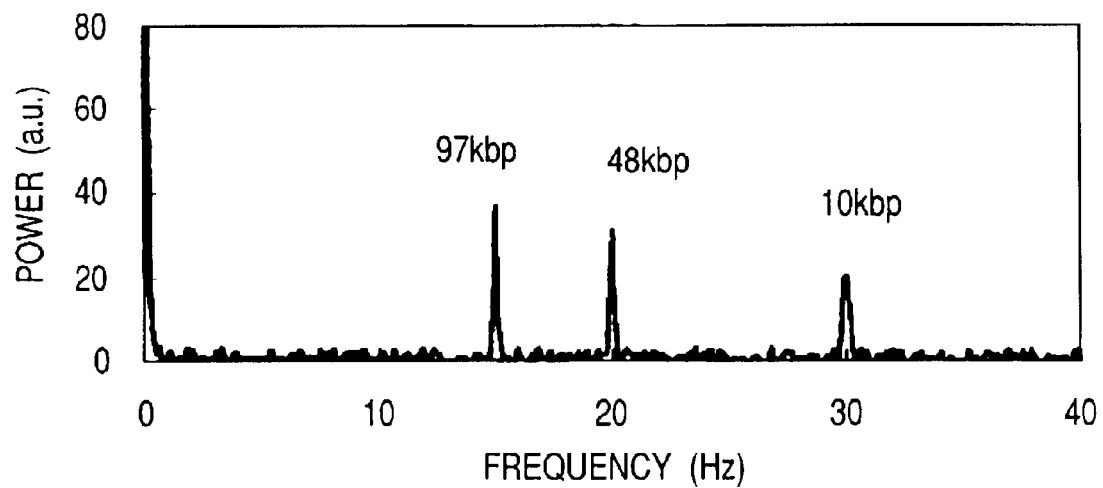
FIGS. 20(A), 20(B) show exemplary results of numerical simulation analyzing a molecular weight marker and genome DNA labeled with TOTO-1 in preferred Embodiment 6 of the present invention.
Figure 20B:
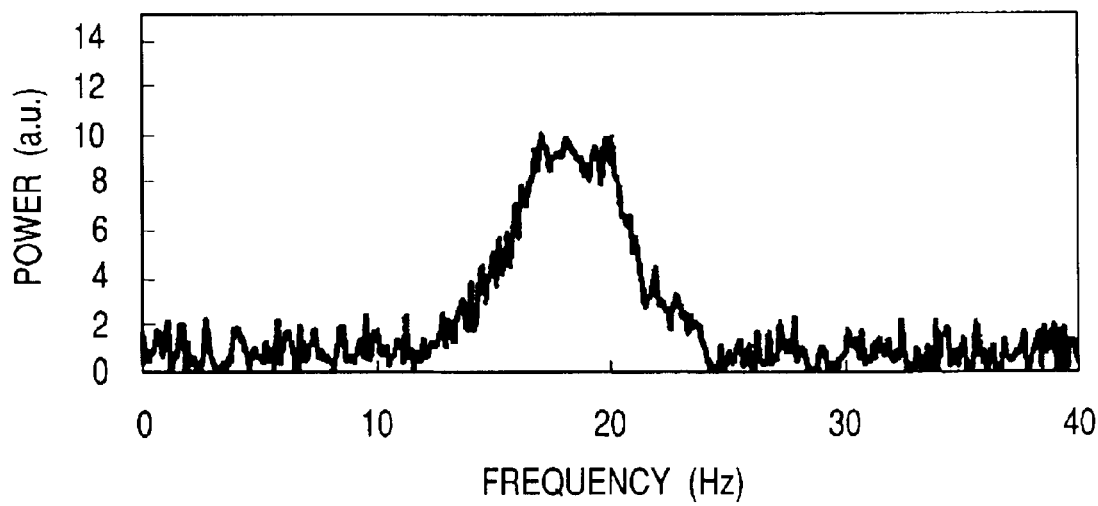

FIG. 20(A) shows the result of numerical simulation using mathematical expressions 3 and 7 for the mixed solution of 10-kbp, 48-kbp, and 97-kbp DNAs, the molecular weight marker, wherein three bands are well separated. FIG. 20(B) shows the result of numerical simulation using mathematical expressions 3 and 7 for the genome DNA solution. Because the genome DNA is not mono-dispersive, unlike the molecular weight marker, the diagram in FIG. 20(B) shows a wide peak spectrum and, consequently, lower SNR as compared with FIG. 20(A). However, it is apparent that genome DNA fragments disperse in length in the range of several tens of kbp to 100 kbp. Thus, the genome DNA checked in Embodiment 6 can be suitably used as a template for PCR.

DNA of several tens of kbp or longer was heretofore analyzed by agarose electrophoresis or the like and it took several tens of minutes to several hours to complete the analysis. According to Embodiment 6, analysis result is obtained within two minutes per sample and analysis time is greatly shortened. In consequence, templates for each PCR are easy to evaluate.

Furthermore, the present invention can also be implemented in such modes as will be specified in items below:

1. An instrument for fluorescence detection comprising a migration channel across which a plurality of charged analytes having different mobility are caused to electophoretically migrate by electric field application in a sieving matrix, a light source emitting excitation light, means for applying excitation light that is controlled to have an intensity profile that periodically changes in the direction that the analytes move to a region across which the analytes disperse in succession in the sieving matrix, and means for detecting fluorescence emission from the analytes.

2. The instrument for fluorescence detection as recited in item 1 further including light-splitting means for splitting the excitation light radiated from a single light source into two diverging beams and characterized in that the above intensity profile is created by making the two beams intersect and interfere with each other in the above region.

3. The instrument for fluorescence detection as recited in item 1 further including means for scanning the above region with the excitation light in cycles of a predetermined frequency in a direction in which to apply the excitation light to the region and means for making the excitation light blink in cycles of a frequency that is an integral multiple of the predetermined frequency.

4. The instrument for fluorescence detection as recited in item 1 further including means for scanning the above region with the excitation light in cycles of a predetermined frequency in a direction in which to apply the excitation light to the region and means for turning the excitation light high and low in cycles of a frequency that is an integral multiple of the predetermined frequency.

5. The instrument for fluorescence detection as recited in item 1 further including an arithmetic unit for calculation to obtain a power spectrum of fluctuation of detected fluorescence intensity.

6. The instrument for fluorescence detection as recited in item 1 characterized in that, when a translational diffusion coefficient of the analytes is represented by D, migration velocity of the analytes V, length of the region irradiated by the excitation light in the migration direction of the analytes L, and pitch of the intensity profile of the excitation light p, p is determined such that $p \neq \pi (DL/V)^{1/2}$.

7. An instrument for fluorescence detection comprising a migration channel across which a plurality of charged analytes having different mobility are caused to electophoretically migrate by electric field application in a sieving matrix, a light source emitting excitation light that is applied to a region across which the analytes disperse in succession in the sieving matrix, lenses for converging a fluorescence image generated by fluorescence emission from the analytes on a slit that is designed to have a transmittance profile that periodically changes in the direction that the analytes move, and a detector for detecting the fluorescence image, wherein the slit is located between the region and the detector.

8. The instrument for fluorescence detection as recited in item 7 further including an arithmetic unit for calculation to obtain a power spectrum of fluctuation of detected fluorescence intensity.

9. The instrument for fluorescence detection as recited in item 7 characterized in that, when a translational diffusion coefficient of the analytes is represented by D, migration velocity of the analytes V, length of the region irradiated by the excitation light in the migration direction of the analytes L, magnifying power of the lenses M, and pitch of the transmittance profile of the slit p, p is determined such that $p \neq \pi M(DL/V)^{1/2}$.

10. An instrument for fluorescence detection comprising a migration channel across which a plurality of charged analytes having different mobility are caused to electophoretically migrate by electric field application in a sieving matrix, a light source emitting excitation light that is applied to a region across which the analytes disperse in succession in the sieving matrix, an array sensor having a plurality of pieces (assumed to be N) of photoelectric elements arranged in the direction that the analytes move and detecting an fluorescence image generated by fluorescence emission from the analytes, and an arithmetic unit for obtaining the sum of products $Q=\Sigma q_i f(Ki)$ for i=1, 2, ..., N, where $q_i$ denotes fluorescence intensity detected by the i-th one of the photoelectric elements arranged in the migration direction and f (Ki) is a function of predetermined pitch where K is a constant including an absolute value of 1 and i is a variable.

11. The instrument for fluorescence detection as recited in item 10 characterized in that the arithmetic unit executes calculation to obtain a power spectrum as a value of Q in the aggregate of the photoelectric elements.

12. The instrument for fluorescence detection as recited in item 10 characterized in that, when a translational diffusion coefficient of the analytes is represented by D, migration velocity of the analytes V, length of the region irradiated by the excitation light in the migration direction of the analytes L, pitch of intervals at which the photoelectric elements are arranged $p_1$, magnifying power of the fluorescence image to be detected M, and pitch of the function of predetermined pitch f (Ki) is $p_2$, $p_1 p_2$ is determined such that $p_1 p_2 \neq \pi M(DL/V)^{1/2}$.

13. The instrument for fluorescence detection as recited in item 10 further including a plurality of migration channels placed in parallel on a same plane at least in part thereof and the parallel migration channels are irradiated orthogonally by the excitation light.

14. An instrument for fluorescence detection comprising a plurality of migration channels placed in parallel on a same plane at least in part thereof, across each of which a plurality of charged analytes having different mobility are caused to electophoretically migrate by electric field application in a sieving matrix, a light source emitting excitation light that is applied to a region across which the analytes disperse in succession in the sieving matrix, a two-dimensional detector having a plurality of pieces (assumed to be N) of photoelectric elements arranged in the direction that the analytes move and detecting an fluorescence image generated by fluorescence emission from the analytes passing through the parallel migration channels that are irradiated orthogonally by the excitation light, and an arithmetic unit for obtaining a power spectrum in the aggregate of the photoelectric elements in such a manner that, when fluorescence intensity detected by the i-th one of the photoelectric elements arranged in the migration direction is represented by qi and a function of predetermined pitch is f (Ki) where K is a constant including an absolute value of 1 and i is a variable, the sum of products $Q=\Sigma q_i f(Ki)$ for i=1, 2, ..., N is calculated.

15. An instrument for fluorescence detection comprising a plurality of migration channels placed in parallel on a same plane at least in part thereof, across each of which a plurality of charged analytes having different mobility are caused to electophoretically migrate by electric field application in a sieving matrix, a light source emitting excitation light that is applied to a region across which the analytes disperse in succession in the sieving matrix, a two-dimensional detector which consists of $N_2$ ($N_2 \geq 2$) arrays arranged in a direction intersecting orthogonally the direction that the analytes move, each array consisting of N1 (N1≧2) pieces of photoelectric elements arranged in the direction that the analytes move, and detects an fluorescence image generated by fluorescence emission from the analytes passing through the parallel migration channels that are irradiated orthogonally by the excitation light, lenses for converging the fluorescence image on area where the photoelectric elements are arranged, and an arithmetic unit for obtaining a power spectrum in the aggregate of the photoelectric elements in such a manner that, when fluorescence intensity detected by one of the two-dimensionally arranged photoelectric elements that is placed in the i-th position in the direction that the analytes move and the j-th position in the direction intersecting orthogonally the direction that the analytes move is represented by $q_{ij}$ and a function of predetermined pitch is f (Ki) where K is a constant including an absolute value of 1 and i is a variable, the sum of products $Q=\Sigma q_{ij}$ for i and j that fulfill constraints $1 \leq i \leq N_1$ and $n_1 \leq j \leq n_2$, where $n_1$ and $n_2$ are integers fulfilling constraint $1 \leq n_1$ &1t; $n_2 \leq N_2$, is calculated.

The present invention makes it unnecessary to spatially separate analytes of a plurality of species during electrophoresis, which would otherwise be required in the previous electrophoresis method. Florescence detection according to the invention is not affected by electrophoresis and separation degradation due to band broadening of analytes injected into the sample injection end of a migration channel. Significantly shorter migration channels and shorter analysis time can be achieved and downsized and lighter instruments for florescence detection can be made. Injection of analytes in narrow bandwidth is not necessary and analysis can be performed by simply injecting sample analytes. It is sufficient to make analytes electophoretically migrate through a channel only for a short while so that the analytes will disperse in succession in the detection region. The migration channel can be shortened as long as the detection region irradiated by excitation light and fluorescence from the analytes in this region is detected. The power supply required for electrophoresis is low voltage. Furthermore, The invention is applicable in a wide range of analyte concentration, not restricting analyte concentration to super dilute concentration that is ideal for unimolecular detection.

What is claimed is:

1. A method for fluorescence detection comprising:

making a plurality of charged analytes having different mobility electophoretically migrate by electric field application in an electrophoretic medium;

applying an excitation light controlled to have an intensity profile that periodically changes in a direction that said analytes move to a region across which said analytes disperse in succession in said electrophoretic medium; and detecting fluorescence emitted from said analytes.

2. A method for fluorescence detection as recited in claim 1, wherein said excitation light radiated from a single light source is split into two diverging beams and said intensity profile is created by making said two beams intersect and interfere with each other in said region.

3. A method for fluorescence detection as recited in claim 1, wherein said region is scanned with said excitation light in cycles of a predetermined frequency in a direction in which to apply the excitation light to the region and said excitation light is controlled to blink in cycles of a frequency that is an integral multiple of said predetermined frequency.

4. A method for fluorescence detection as recited in claim 1, wherein a power spectrum of fluctuation of intensity of said fluorescence is obtained.

5. A method for fluorescence detection as recited in claim 1, wherein, when a translational diffusion coefficient of said analytes is represented by D, migration velocity of said analytes V, length of said region irradiated by said excitation light in the migration direction of said analytes L, and pitch of said intensity profile of said excitation light p, p is determined such that $p \neq \pi (DL/V)^{1/2}$.

* * * * *